United States Patent [19]
Singh et al.

[11] Patent Number: 6,002,000
[45] Date of Patent: *Dec. 14, 1999

[54] CHEMILUMINESCENT COMPOUNDS AND METHODS OF USE

[75] Inventors: Sharat Singh, San Jose; Rajendra Singh, Mountain View, both of Calif.; Frank Meneghini, Keene, N.H.; Edwin F. Ullman, Atherton, Calif.

[73] Assignee: Dade Behring Marburg GmbH, Marburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/661,849

[22] Filed: Jun. 11, 1996

Related U.S. Application Data

[62] Division of application No. 08/373,678, Jan. 17, 1995, Pat. No. 5,545,834, which is a continuation of application No. 07/916,453, Jul. 20, 1992, abandoned.

[51] Int. Cl.$^6$ .................. C07D 498/10; C07D 513/10; C09K 11/06
[52] U.S. Cl. .................. 544/6; 544/71; 546/18; 252/301.16; 252/301.26; 252/301.32; 252/700
[58] Field of Search .......................... 544/6, 71

[56] References Cited

U.S. PATENT DOCUMENTS

| | | | |
|---|---|---|---|
| 3,876,659 | 4/1975 | Houlihan et al. | 260/326.1 |
| 4,380,580 | 4/1983 | Boguslaski et al. | 435/7 |
| 4,383,031 | 5/1983 | Boguslaski et al. | 435/7 |
| 4,729,950 | 3/1988 | Kricka et al. | 435/28 |
| 4,857,652 | 8/1989 | Schaap | 549/510 |
| 4,891,324 | 1/1990 | Pease et al. | 436/519 |
| 4,931,223 | 6/1990 | Bronstein et al. | 252/700 |
| 4,950,588 | 8/1990 | Dattagupta | 435/6 |
| 4,959,182 | 9/1990 | Schaap | 252/700 |
| 4,962,192 | 10/1990 | Schaap | 536/18.1 |
| 5,013,827 | 5/1991 | Schaap | 536/17.3 |
| 5,055,414 | 10/1991 | Babb et al. | 436/501 |
| 5,068,339 | 11/1991 | Schaap et al. | 548/110 |
| 5,154,887 | 10/1992 | Babb et al. | 422/56 |
| 5,225,584 | 7/1993 | Brooks et al. | 558/189 |
| 5,283,334 | 2/1994 | McCapra | 546/104 |
| 5,284,951 | 2/1994 | McCapra et al. | 546/107 |
| 5,290,936 | 3/1994 | Beheshti et al. | 546/104 |
| 5,338,847 | 8/1994 | McCapra | 546/104 |
| 5,438,146 | 8/1995 | Schaap et al. | 548/110 |
| 5,516,636 | 5/1996 | McCapra | 435/6 |
| 5,536,834 | 7/1996 | Singh et al. | 544/98 |
| 5,545,834 | 8/1996 | Singh et al. | 546/6 |
| 5,578,498 | 11/1996 | Singh et al. | 436/518 |
| 5,593,845 | 1/1997 | Akhavan-Tafti et al. | 435/7.9 |
| 5,616,729 | 4/1997 | Schaap et al. | 549/223 |
| 5,631,353 | 5/1997 | Schaap et al. | 536/4.1 |
| 5,652,345 | 7/1997 | Schaap et al. | 536/4.1 |
| 5,670,644 | 9/1997 | Akhavan-Tafti et al. | 546/103 |
| 5,672,478 | 9/1997 | Singh et al. | 435/6 |
| 5,698,728 | 12/1997 | Schaap et al. | 556/448 |
| 5,750,698 | 5/1998 | Akhavan-Tafti et al. | 546/102 |

FOREIGN PATENT DOCUMENTS

| | | |
|---|---|---|
| 270946A2 | 6/1988 | European Pat. Off. . |
| 322926A2 | 7/1989 | European Pat. Off. . |
| 324202A1 | 7/1989 | European Pat. Off. . |
| 352713B1 | 7/1989 | European Pat. Off. . |
| 330433A2 | 8/1989 | European Pat. Off. . |
| 345776A3 | 12/1989 | European Pat. Off. . |
| WO 8912232 | 12/1989 | WIPO . |
| WO 9007511 | 7/1990 | WIPO . |
| WO 9506877 | 3/1995 | WIPO . |

OTHER PUBLICATIONS

Hammond et al.; *J Biolum and Chemilum*;; Nucleophilic Addition to the 9 Position of 9–Phenylcarboxylate–10–methylacridinium Protects against Hydrolysis of the Ester; 1990.

Zomer et al.; *Analytica Chimica Acta*: 227:11–19; Chemiluminogenic Labels, Old and New; 1989.

Lee et al; *J of Amer Chem Soc*; 102:11; pp. 3823–3829; Structural Effects on the Intramolecular Electron Transfer Induced Decomposition of a Series of 1,2,–Dioxetanes Derived from 9–Alkylidene–10–methylacridans; May 21, 1980.

McCapra et al; *Tetrahedron Letters*; 23:49; pp. 5225–5229; Metal Catalysed Light Emission from a Dioxetan; 1982.

McCapra, et al.; *J. Biolum and Chemilum*; 4:51–58; Luminescent Labels for Immunoassay—From Concept to Practice; 1989.

Turro et al; *J Amer Chem Soc*; 100:22; Generation, Diffusivity, and Reactivity of Singlet Oxygen in Polymer Matrices. A Convenient and Sensitive Chemiluminescent Technique; Oct. 25, 1978.

Lee et al; *J of Organic Chem*; 41:16; pp. 2685–2688; Chemiluminescence from the Reaction of Singlet Oxygen with 10,10'–dimethyl–9,9'–biacridylidene. A Reactive 1,2–dioxethan; 1976.

Weeks et al; *Clin. Chem.*; 29/8; 1474–1479; Acridinium Esters as High–Specific–Activity Labels in Immunoassay; 1983.

*Primary Examiner*—John M. Ford
*Assistant Examiner*—Bruck Kifle
*Attorney, Agent, or Firm*—Theodore J Leitereg

[57] ABSTRACT

Methods are disclosed for determining an analyte in a medium suspected of containing the analyte. One method comprises providing (1) combining a medium suspected of containing the analyte and a novel chemiluminescent compound, (2) combining a means for chemically activating the chemiluminescent compound; and (3) detecting the amount of luminescence generated by the chemiluminescent compound. The amount of luminescence generated is related to the amount of analyte in the medium. The chemiluminescent compound can be chemically activated by hydrogen peroxide. Compositions and kits are also disclosed.

11 Claims, 3 Drawing Sheets

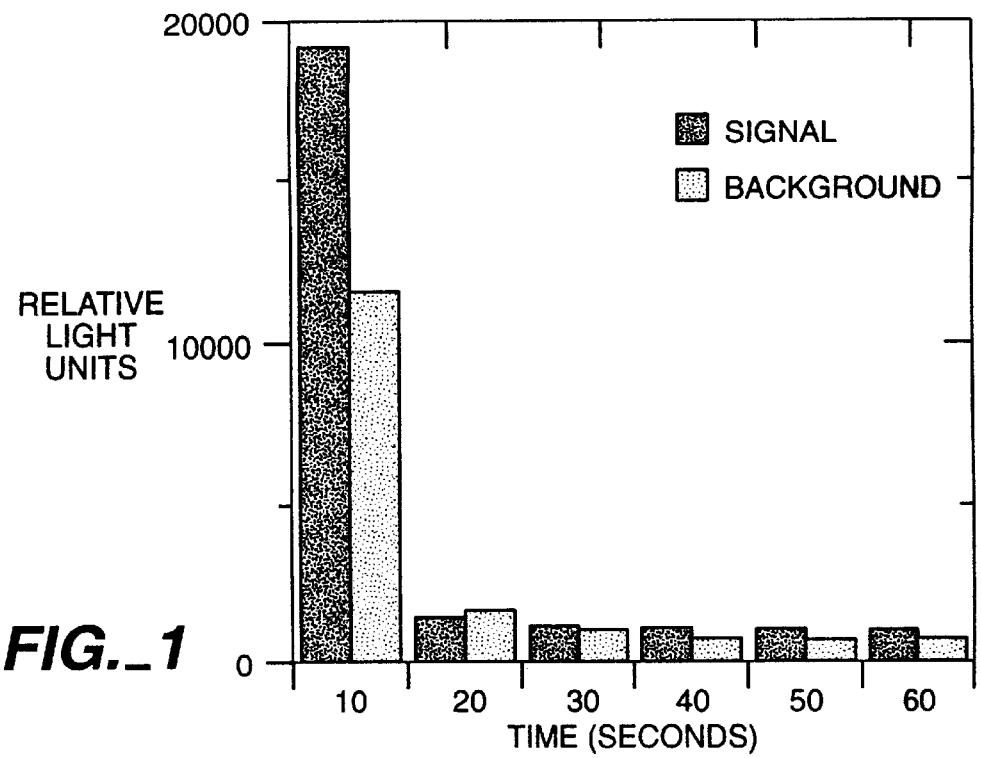
FIG._1
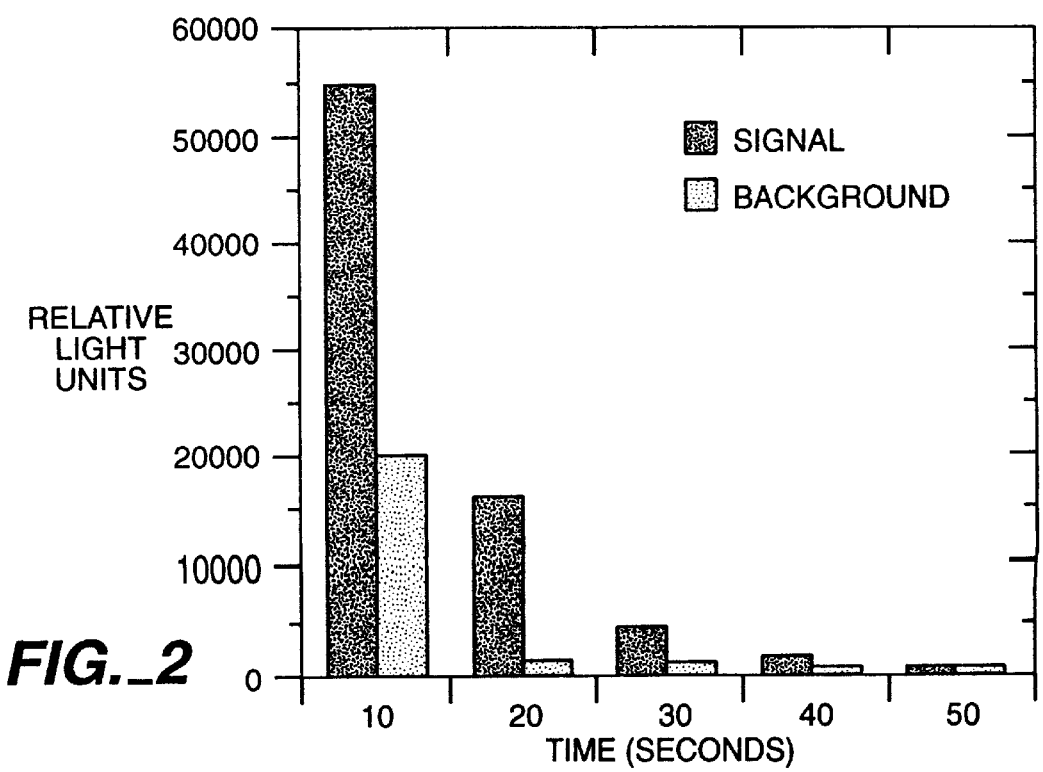
FIG._2

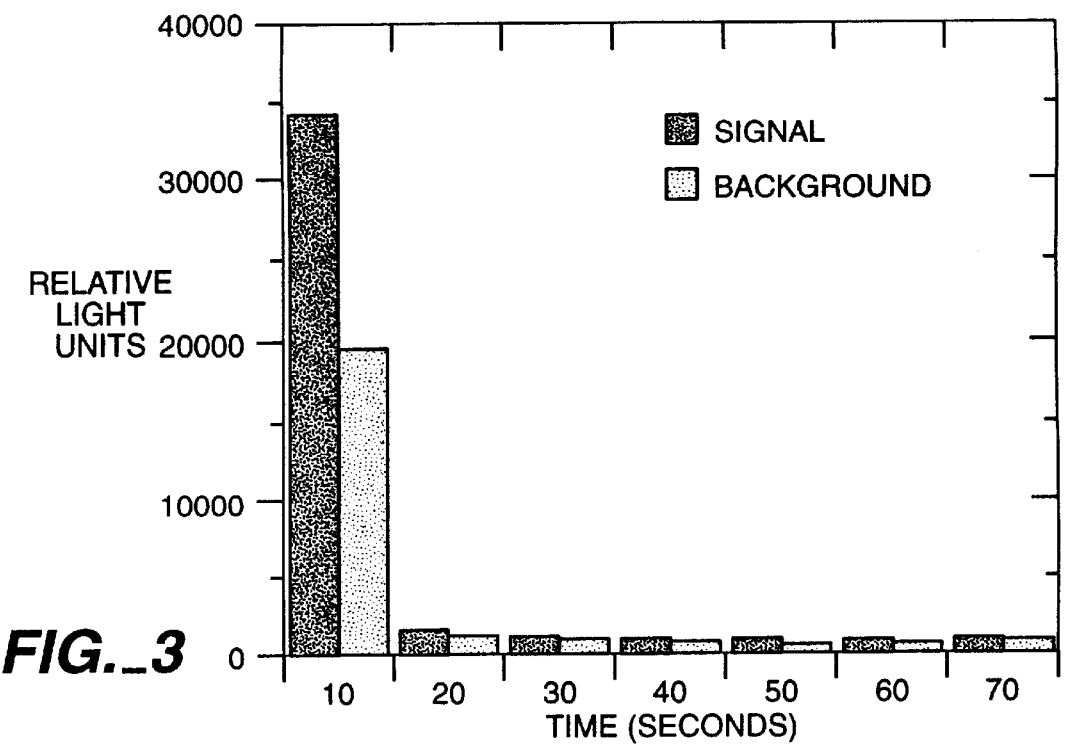
FIG._3
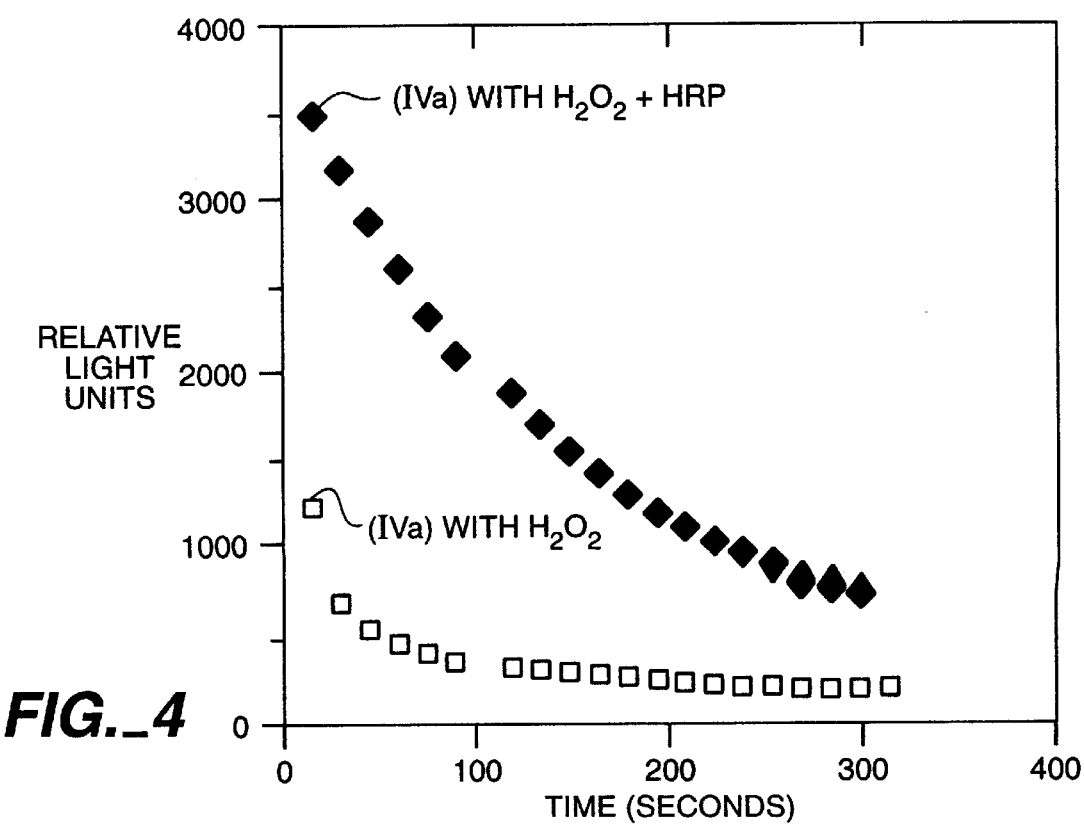
FIG._4

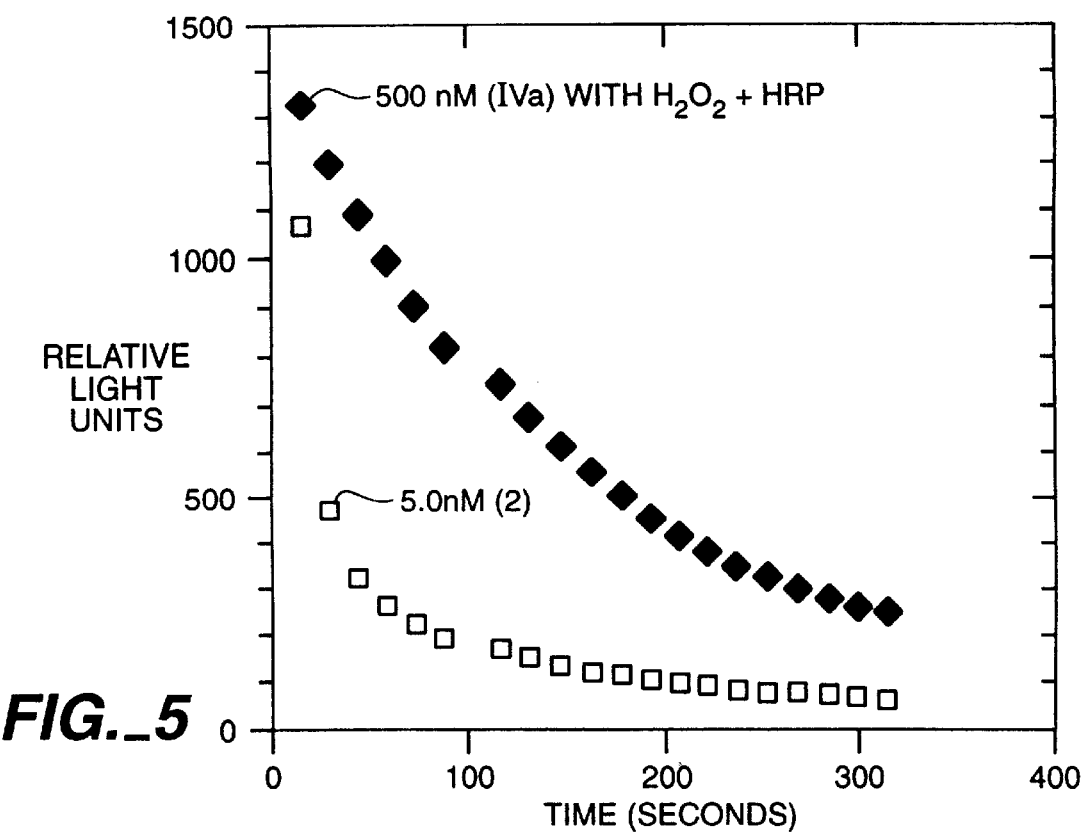
FIG._5

CHEMILUMINESCENT COMPOUNDS AND METHODS OF USE

This application is a division of patent application U.S. Ser. No. 08/373,678 filed Jan. 17, 1995, now U.S. Pat. No. 5,545,834, which is a continuation of patent application U.S. Ser. No. 07/916,453 filed Jul. 20, 1992, now abandoned.

BACKGROUND OF THE INVENTION

Field of the Invention

This invention relates to compositions, methods and kits for determining an analyte in a sample.

Chemiluminescent labels for immunoassays and nucleic acid probe assays provide a high degree of sensitivity when compared to other commonly used labels. An excellent overview of the subject is discussed in McCapra, et al., *Journal of Bioluminescence and Chemiluminescence* 4:51–58 (1989).

Particularly important chemiluminescent compounds are acridinium esters and amides, which must be stored in water at a pH that is compatible with protein stability requirements. This results in the formation of a pseudobase, which is not chemiluminescent. Chemiluminescence is initiated by adding acid to form the acridinium salt, followed by the addition of strongly alkaline hydrogen peroxide. In general, these conditions are not ideal for immunoassays as they are not suitable for preserving receptor-ligand binding and are undesirably complex.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is increased by the relatively small sample sizes that can be utilized.

In developing an assay there are many considerations. one consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of the analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with different labels where the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays have previously been described for small molecules. These assays include Syva Company's FRAT® assay, EMIT® assay, enzyme channeling immunoassay, and fluorescence energy transfer immunoassay (FETI); enzyme inhibitor immunoassays (Hoffman LaRoche and Abbott Laboratories); and fluorescence polarization immunoassay (Dandlicker), among others. All of these methods have limited sensitivity, and only a few including FETI and enzyme channeling, are suitable for large multiepitopic analytes.

Chemiluminescent compounds find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Chemiluminescent labels have been described for immunoassays and nucleic acid assays where a group, which is covalently bound to a binding partner, on chemical activation emits light. A nucleic acid assay kit utilizing an acridinium ester is sold by Genprobe (Pace 2 system®, San Diego, Calif.) and MagicLite® immunoassay kits using this type of label are sold by Ciba-Geigy (Basel, Switzerland).

Although, chemiluminescent labels have the advantage of offering exceptional sensitivity in ligand binding assays, one or more chemical activation steps are usually needed. Therefore, there is a need for novel chemiluminescent compounds that do not require several activation steps.

Brief Description of the Related Art

U.S. Pat. No. 3,876,659 discloses novel spiro tricyclic isoindolines.

U.S. Pat. Nos. 4,380,580 and 4,383,031, respectively, describe heterogeneous and homogeneous chemiluminescent specific binding assays.

U.S. Pat. No. 4,891,324 describes the use of a particle with a luminescer in assays.

European Patent Application 0 270 946 A2 pertains to chromogenic acridinone enzyme substrates useful in the detection of enzymes.

European Patent Application 0 322 926 A2 describes assays utilizing improved chemiluminescent esters, thioesters, and amides.

European Patent Application 0 324 202 A1 discloses acridinium compounds as chemiluminogenic labels.

European Patent Application 0 421 788 A2 describes a haloperoxidase-acid-optimum chemiluminescence assay system for determining the presence or amount of an analyte in a liquid sample. The system utilizes haloperoxidase, a halide, an oxidant and a chemiluminigenic substrate.

PCT 88/00695 describes the use of dioxetanes in assays, where the dioxetanes contain an enzyme-cleavable group, the removal of which results in a negatively charged substituent being bonded to the dioxetane. This causes the dioxetane to decompose to form a luminescent substance.

Heller, et al. describe chemiluminescent and fluorescent probes for DNA hybridization systems in "Rapid Detection and Identification of Infectious Agents" Academic Press, Inc., pages 245–257 (1985).

Zomer, et al. describe chemiluminogenic labels in *Analytica Chimica Acta* 227:11–19 (1989).

SUMMARY OF THE INVENTION

The present invention concerns spiro-acridan chemiluminescent compounds.

These compounds are useful in light emitting chemical compositions containing the instant compounds and hydrogen peroxide.

These chemiluminescent compounds also find particular utility in methods for determining an analyte. A sample suspected of containing the analyte is combined in an assay medium with one of the present chemiluminescent compounds, which may be bound to an sbp member, where the sbp member binds the analyte or a second sbp member to form a complex related to the presence of the analyte. The chemiluminescent compound is activated, for example, by hydrogen peroxide. The amount of luminescence generated is then detected and related to the amount of analyte in the sample.

Kits comprising the present chemiluminescent compounds are also included in the invention.

BRIEF DESCRIPTION OF THE DRAWING

The invention will be described in further detail with reference to the accompanying drawings, wherein:

FIG. 1 is a graph showing the chemiluminescent decay of Compound (Ic) from Example 7.

FIG. 2 is a graph showing the chemiluminescent decay of Compound (IIa) from Example 7.

FIG. 3 is a graph showing the chemiluminescent decay of Compound (IIIa) from Example 7.

FIG. 4 is a graph showing the chemiluminescence of Compound (IVa) from Example 9.

FIG. 5 is a graph showing the chemiluminescence of Compound (IVa) and (2) from Example 9.

DESCRIPTION OF THE SPECIFIC EMBODIMENTS

As mentioned above, the present invention concerns chemiluminescent compounds that can be chemically activated to a luminescent product and the use of these compounds as a label. The chemiluminescent compound may be associated with a member of a specific binding pair and this reagent is utilized as a labeled reagent in assays for the detection of an analyte. Chemical activation is achieved by hydrogen peroxide, for example. The labels of the present invention can be used in both homogeneous and heterogeneous assay protocols to determine an analyte. In the assay protocol the components are combined and the light produced is a function of analyte concentration.

Before proceeding further with a description of the specific embodiments of the present invention, a number of terms will be defined and described in detail.

Analyte: the compound or composition to be detected. The analyte can be a member of a specific binding pair ("sbp") and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

Polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight. Among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure: protamines, histones, albumins, globulins, scleroproteins, phosphoproteins, mucoproteins, chromoproteins, lipoproteins, nucleoproteins, glycoproteins, T-cell receptors, proteoglycans, HLA, and unclassified proteins such as somatotropin, prolactin, insulin and pepsin.

A number of proteins found in the human plasma are important clinically and include: prealbumin, albumin, $\alpha_1$-lipoprotein, $\alpha_1$-antitrypsin, $\alpha_1$-glycoprotein, transcortin, 4.6S-postalbumin, tryptophan-poor $\alpha_1$-glycoprotein, $\alpha_1\chi$-glycoprotein, thyroxin-binding globulin, inter-$\alpha$-trypsin-inhibitor, Gc-globulin (Gc 1-1, Gc 2-1 and Gc 2-2), Haptoglobin (Hp 1-1, Hp 2-1 and Hp 2-2), ceruloplasmin, cholinesterase, $\alpha_2$-lipoprotein(s), myoglobin, C-reactive protein, $\alpha_2$-macroglobulin, $\alpha_2$-HS-glycoprotein, Zn-$\alpha_2$-glycoprotein, $\alpha_2$-neuramino-glycoprotein, erythropoietin, $\beta$-lipoprotein, transferrin, hemopexin, fibrinogen, plasminogen, $\beta_2$-glycoprotein I and $\beta_2$-glycoprotein II, Immunoglobulin G (IgG) or $\gamma$G-globulin (Mol. formula: $\gamma_2\kappa_2$ or $\gamma_2\lambda_2$), Immunoglobulin A (IgA) or $\gamma$A-globulin (Mol. formula: $(\alpha_2\kappa_2)^n$ or $(\alpha_2\lambda_2)^n$), Immunoglobulin M (IgM) or $\gamma$M-globulin (Mol. formula: $(\mu_2\kappa_2)^5$ or $(\mu_2\lambda_2)^5$), Immunoglobulin D (IgD) or $\gamma$D-Globulin ($\gamma$D) (Mol. formula: $\delta_2\kappa_2$ or $\delta_2\lambda_2$), Immunoglobulin E (IgE) or $\gamma$E-Globulin ($\gamma$E) (Mol. formula: $\epsilon_2\kappa_2$ or $\kappa_2\lambda_2$), free $\kappa$ and $\lambda$ light chains, and complement factors (C'l, including C'lq, C'lr and C'ls; C'2; C'3, including $\beta_1$A and $\alpha_2$D; C'4; C'5; C'6; C'7; C'8; and C'9).

Important blood clotting factors (International designation) include: fibrinogen (I), prothrombin (II), thrombin (IIa), tissue thromboplastin (III), proaccelerin/accelerator globulin (V and VI), proconvertin (VII), antihemophilic globulin (VIII), Christmas factor/plasma thromboplastin component (IX), Stuart-Prower factor/autoprothrombin III (X), plasma thromboplastin antecedent (XI), Hagemann factor (XII) and fibrin-stabilizing factor (XIII).

Important protein hormones include: peptide and protein hormones such as parathyroid hormone (parathromone), thyrocalcitonin, insulin, glucagon, relaxin, erythropoietin, melanotropin (melanocyte-stimulating hormone;

intermedin), somatotropin (growth hormone), corticotropin (adrenocortico-tropic hormone), thyrotropin, follicle-stimulating hormone, luteinizing hormone (interstitial cell-stimulating hormone), luteomammotropic hormone (luteotropin, prolactin), gonadotropin (chorionic gonadotropin); tissue hormones such as secretin, gastrin, angiotensin I and II, bradykinin and human placental lactogen; cytokines such as IL I, IL II, IL VI, EGF, TNF and NGF; cancer antigens such as PSA, CEA, α-fetoprotein, acid phosphatase, CA 19.9 and CA 125; tissue specific antigens such as alkaline phosphatase, myoglobin, CPK-MB, calcitonin and myelin basic protein; and peptide hormones from the neurohypophysis such as oxytocin, vasopressin, and Releasing factors (CRF, LRF, TRF, Somatotropin-RF, GRF, FSH-RF, PIF and MIF).

Other polymeric materials of interest are mucopolysaccharides and polysaccharides.

Illustrative antigenic polysaccharides derived from microorganisms are as follows:

| Species of Microorganisms | Hemosensitinin Found in |
|---|---|
| Streptococcus pyogenes | Polysaccharide |
| Diplococcus pneumoniae | Polysaccharide |
| Neisseria menigitidis | Polysaccharide |
| Neisseria gonorhoeae | Polysaccharide |
| Corynebacterium diphtheriae | Polysaccharide |
| Actinobacillus mallei | Crude extract |
| Actinobacillus | |
| Francisella tularenis | Lipopolysaccharide, Polysaccharide |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenese | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhimurium | Polysaccharide |
| Salmonella derby | |
| Salmonella pullorum | |
| Shigella dysenteriae | Polysaccharide |
| Shigella flexneri | |
| Shigella sonnei | Crude, polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
    *Corynebacterium diphtheriae*
Pneumococci
    *Diplococcus pneumoniae*
Streptococci
    *Streptococcus pyogenes*
    *Streptococcus salivarus*
Staphylococci
    *Staphylococcus aureus*
    *Staphylococcus albus*
Neisseriae
    *Neisseria meningitidis*
    *Neisseria gonorrhoea*
Enterobacteriaceae
    The coliform bacteria
        *Escherichia coli*
        *Aerobacter aerogenes*
        *Klebsiella pneumoniae*
    The Salmonellae
        *Salmonella typhosa*
        *Salmonella choleraesuis*
        *Salmonella typhimurium*
    The Shigellae
        *Shigella dysenteriae*
        *Shigella schmitzii*
        *Shigella arabinotarda*
        *Shigella flexneri*
        *Shigella boydii*
        *Shigella sonnei*
Other enteric bacilli
    Proteus species
        *Proteus vulgaris*
        *Proteus mirabilis*
        *Proteus morgani*
    *Pseudomonas aeruginosa*
    *Alcaligenes faecalis*
    *Vibrio cholerae*
Hemophilus-Bordetella group
    *Hemophilus influenzae*
        *H. ducreyi*
        *H. hemophilus*
        *H. aegypticus*
        *H. parainfluenzae*
    *Bordetella pertussis*
Pasteurellae
    *Pasteurella pestis*
    *Pasteurella tulareusis*
Brucellae
    *Brucella melitensis*
    *Brucella abortus*
    *Brucella suis*
Aerobic Spore-forming Bacilli
    *Bacillus anthracis*
    *Bacillus subtilis*
    *Bacillus megaterium*
    *Bacillus cereus*
Anaerobic Spore-forming Bacilli
    *Clostridium botulinum*
    *Clostridium tetani*
    *Clostridium perfringens*
    *Clostridium novyi*
    *Clostridium septicum*
    *Clostridium histolyticum*
    *Clostridium tertium*
    *Clostridium bifermentans*
    *Clostridium sporogenes*
Mycobacteria
    *Mycobacterium tubercolosis hominis*
    *Mycobacterium bovis*
    *Mycobacterium avium*
    *Mycobacterium leprae*
    *Mycobacterium paratuberculosis*
Actinomycetes (fungus-like bacteria)
    *Actinomyces israelii*
    *Actinomyces bovis*
    *Actinomyces naeslundii*
    *Nocardia asteroides*
    *Nocardia brasiliensis*
The Spirochetes
    *Treponema pallidium*
    *Treponema pertenue*
    *Treponema carateum*
    *Borrelia recurrentis*
    *Leptospira icterohemorrhagiae*
    *Leptospira canicola*

*Spirillum minus*
  *Streptobacillus moniliformis*
Trypanosomas
Mycoplasmas
  *Mycoplasma pneumoniae*
Other pathogens
  *Listeria monocytogenes*
  *Erysipelothrix rhusiopathiae*
  *Streptobacillus monilformis*
  *Donvania granulomatis*
  *Bartonella bacilliformis*
Rickettsiae (bacteria-like parasites)
  *Rickettsia prowazekii*
  *Rickettsia mooseri*
  *Rickettsia rickettsiae*
  *Rickettsia conori*
  *Rickettsia australis*
  *Rickettsia sibiricus*
  *Rickettsia akari*
  *Rickettsia tsutsugamushi*
  *Rickettsia burnetii*
  *Rickettsia quintana*
Chlamydia (unclassifiable parasites bacterial/viral)
  Chlamydia agents (naming uncertain)
Fungi
  *Cryptococcus neoformans*
  *Blastomyces dermatidis*
  *Histoplasma capsulatum*
  *Coccidioides immitis*
  *Paracoccidioides brasiliensis*
  *Candida albicans*
  *Aspergillus fumigatus*
  *Mucor corymbifer (Absidia corymbifera)*
  Phycomycetes
    *Rhizopus oryzae*
    *Rhizopus arrhizus*
    *Rhizopus nigricans*
  *Sporotrichum schenkii*
  *Fonsecaea pedrosoi*
  *Fonsecaea compacta*
  *Fonsecaea dermatidis*
  *Cladosporium carrionii*
  *Phialophora verrucosa*
  *Aspergillus nidulans*
  *Madurella mycetomi*
  *Madurells grisea*
  *Allescheria boydii*
  *Phialosphora jeanselmei*
  *Microsporum gypseum*
  *Trichophyton mentagrophytes*
  *Keratinomyces ajelloi*
  *Microsporum canis*
  *Trichophyton rubrum*
  *Microsporum adouini*
Viruses
Adenoviruses
Herpes Viruses
  Herpes simplex
  Varicella (Chicken pox)
  Herpes Zoster (Shingles)
  Virus B
  Cytomegalovirus
Pox Viruses
  Variola (smallpox)
  Vaccinia
  *Poxvirus bovis*
  Paravaccinia
  *Molluscum contagiosum*
Picornaviruses
  Poliovirus
  Coxsackievirus
  Echoviruses
  Rhinoviruses
Myxoviruses
  Influenza (A, B, and C)
  Parainfluenza (1–4)
  Mumps Virus
  Newscastle Disease Virus
  Measles Virus
  Rinderpest Virus
  Canine Distemper Virus
  Respiratory Syncytial Virus
  Rubella Virus
Arboviruses
  Eastern Equine Encephalitis Virus
  Western Equine Encephalitis Virus
  Sindbis Virus
  Chikungunya Virus
  Semliki Forest Virus
  Mayora Virus
  St. Louis Encephalitis Virus
  California Encephalitis Virus
  Colorado Tick Fever Virus
  Yellow Fever Virus
  Dengue Virus
Reoviruses
  Reovirus Types 1–3
Retroviruses
  Human Immunodeficiency Viruses I and II (HIV)
  Human T-cell Lymphotrophic Virus I & II (HTLV)
Hepatitis
  Hepatitis A Virus
  Hepatitis B Virus
  Hepatitis C Virus
Tumor Viruses
  Rauscher Leukemia Virus
  Gross Virus
  Maloney Leukemia Virus
  Human Papilloma Virus The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids: morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; and diterpene alkaloids, their derivatives and metabolites.

The next group of drugs includes steroids, which includes the estrogens, gestrogens, androgens, adrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, for example, phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and derivatives and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progesterone, polypeptides such as angiotensin, LHRH, and immunosuppressants such as cyclosporin, FK-506, mycophenolic acid, and so forth.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is the tricyclic anti-depressants, which include imipramine, dismethylimipramine, amitriptyline, nortriptyline, protriptyline, trimipramine, chlomipramine, doxepine, and desmethyldoxepin, The next group of drugs are the antineoplastics, which include methotrexate.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamycin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Analyte analog or ligand analog ("analog"): a modified analyte or analyte surrogate, modified ligand or ligand surrogate, or organic radical, usually of a molecular weight greater than 100, which can compete with the analogous analyte or ligand for binding to a receptor, the modification providing means to join the analog to another molecule. The term analyte surrogate or ligand surrogate refers to a compound having the capability of specifically binding a receptor complementary to the analyte or ligand. The analog will usually, but not always, differ from the analyte or ligand by more than replacement of a hydrogen with a bond which links the analog to a hub or label. The analog can bind to the receptor in a manner similar to the analyte or ligand. The analog could be, for example, an antibody directed against the idiotype of an antibody to the ligand.

Member of a specific binding pair ("sbp member"): one of two different molecules, having an area on the surface or in a cavity which specifically binds to and is thereby defined as complementary with a particular spatial and polar organization of the other molecule. The members of the specific binding pair can be referred to as ligand and receptor (antiligand) such as when they are members of an immunological pair such as antigen-antibody and hapten-antibody. Other specific binding pairs which are not immunological pairs, are also included in this invention, for example, enzyme-substrate, biotin-avidin, hormones-hormone receptors, nucleic acid duplexes, IgG-protein A, polynucleotide pairs such as DNA-DNA, DNA-RNA.

Ligand: any organic compound for which a receptor naturally exists or can be prepared, and includes antigens and haptens.

Antigen: any compound capable of binding to an antibody and against which antibodies can be raised.

Hapten: any compound capable of binding specifically to an antibody, but which does not itself act as an immunogen (or antigen) for preparation of the antibodies. Antibodies which recognize a hapten can be prepared against compounds comprised of the hapten linked to an immunogenic (or antigenic) carrier.

Receptor ("antiligand"): any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Antibody: an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Polynucleotide: a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Alkyl group: a monovalent branched or unbranched radical derived from an aliphatic hydrocarbon by removal of one H atom and includes both lower alkyl and upper alkyl groups. Lower alkyl groups contain from 1 to 5 carbon atoms such as, e.g., methyl, ethyl, propyl, butyl, isopropyl, isobutyl, pentyl, isopentyl, etc. Upper alkyl groups contain more than 6 carbon atoms, usually 6 to 20 carbon atoms, such as, e.g., hexyl, heptyl, octyl, etc.

Aryl group: an organic radical derived from an aromatic hydrocarbon by the removal of one atom and containing one or more aromatic rings, usually one to four aromatic rings, such as, e.g., phenyl (from benzene), naphthyl (from naphthalene), etc.

Substituted: when a hydrogen atom of a molecule has been replaced by another atom, which may be a single atom such as a halogen, etc., or part of a group of atoms forming a functionality such as a substituent or organic radical having from 1 to 50 atoms (other than the requisite hydrogen atoms necessary to satisfy the valencies of such atoms), which atoms are independently selected from the group consisting of carbon (C), oxygen (O), nitrogen (N), sulfur (S) and phosphorus (P), and which may or may not be bound to one or more metal atoms. The O, N, S, or P. if present, are bound to carbon or to one or more of each other or to hydrogen or to a metal atom to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Examples of such organic radicals or groups, by way of illustration and not limitation, are alkyl, alkylidine, aryl, aralkyl, and alkyl, aryl, and aralkyl substituted with one or more of the aforementioned functionalities.

Linking group: the covalent linkage between molecules. The linking group will vary depending upon the nature of the molecules, i.e., chemiluminescent compound, sbp member or molecule associated with or part of a particle, being linked. Functional groups that are normally present or are introduced on a chemiluminescent compound will be employed for linking these materials to an sbp member or a particle such as a lipophilic component of a liposome or oil droplet, latex particle, silicon particle, metal sol, or dye crystallite.

For the most part, carbonyl functionalities will find use, both oxocarbonyl, e.g., aldehyde and non-oxocarbonyl (including nitrogen and sulfur analogs) e.g., carboxy, amidine, amidate, thiocarboxy and thionocarboxy. As used herein, the term "non-oxo-carbonyl" shall include the carbonyl group of carboxylic acids, —COOH; the nitrogen containing iminocarbonyl group of amidic acids, —C(NH)OH; and the sulfur containing thionocarbonyl group of thio acids, —C(S)OH. Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms and more preferably 1 to 20 atoms, each independently selected from the group normally consisting of carbon, oxygen, nitrogen, sulfur and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for the substituent having from 1 to 50 atoms. As a general rule, the length of a particular linking group can be selected arbitrarily to provide for convenience of synthesis and the incorporation of any desired group. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

Conjugate: a molecule comprised of two or more subunits bound together to form a single structure. The binding can be made either by a direct connection (e.g. a chemical bond) between the subunits or by use of a linking group. For example, in one context of the present invention, a ligand conjugated to a chemiluminescent label of this invention, is a ligand-label conjugate. A composition which is described as comprising subunit A conjugated to subunit B is a composition wherein subunit A is bound to subunit B.

Conjugation: any process wherein two subunits are linked together. The conjugation process can be comprised of any number of steps.

Support or surface: a surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.* 245:3059 (1970).

The surface will usually be polyfunctional or be capable of being polyfunctionalized or be capable of binding an oligonucleotide, an sbp member, and/or a chemiluminescent compound through specific, non-specific, covalent or non-covalent interactions. A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds to surfaces is well known and is amply illustrated in the literature. See for example Cuatrecasas, supra. The length of a linking group to the oligonucleotide, sbp member or chemiluminescent compound may vary widely, depending upon the nature of the compound being linked, the effect of the distance between the compound being linked and the surface on the specific binding properties and the like. The sbp member will be substantially bound to the outer surface of the support.

Particles: particles of at least about 20 nm and not more than about 50 microns, usually at least about 40 nm and less than about 25 microns, preferably from about 0.10 to 5.0 microns in diameter, normally having a volume of less than 1 picoliter. The particle may be organic, inorganic, swellable, non-swellable, porous or non-porous, having any density, but preferably having a density approximating water, generally from about 0.7 to about 1.5 g/ml, preferably suspendible in water, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable so as to bind at their surface, either directly or indirectly, an sbp member.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

Label: Any molecule which produces or can be induced to produce a signal. The label may be conjugated to an analyte or an antibody, or to another molecule such as a receptor or a molecule that can bind to a receptor such as a ligand, particularly a hapten. In the subject invention, the label is a member of the signal producing system, as defined below, that includes a signal producing means.

The spiroacridane chemiluminescent compounds of this invention are part of a chromogen system and thus are particularly well-suited as labels. The chemiluminescent compound provides the desired amplification by producing a product, which leads to direct light emission, e.g., chemiluminescence.

Signal Producing System ("sps"): the function of the signal producing system is to produce a product which provides a detectable signal related to the amount of bound and/or unbound label. The sps may have one or more components. The sps includes all of the reagents required to produce a measurable signal including signal producing means capable of interacting with the label to produce a signal.

The signal producing system provides a signal detectable by external means, normally by measurement of electromagnetic radiation, desirably by visual examination. For example, the signal producing system can include a chromophoric substrate and enzyme, where the chromophoric substrate is enzymatically converted to a dye which absorbs light in the ultraviolet or visible region, phosphors or fluorescers.

The signal producing means is capable of interacting with a component of the signal producing system to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

Ancillary Materials: Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially: when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

The spiroacridane chemiluminescent compounds of this invention are derivatives of acridine. These compounds can be made to luminesce at a moderate pH, within the range of 6–10 and preferably within the range of 7–9, upon contact with hydrogen peroxide without prior acidification.

The detectability of the chemiluminescent compounds of this invention is at least comparable to phenyl N-methylacridinium-9-carboxylate, which is one of the most efficient chemiluminescent acridinium salts. The compounds of the present invention are preferred over the use of such acridinium salts as chemiluminescers. When acridinium salts are stored in water as acridinium esters or amides, at a pH that is compatible with protein stability requirements, hydroxide ion adds to form a pseudobase. Chemiluminescence is then not efficiently initiated without first adding acid to reform the acridinium salt, followed by the addition of alkaline hydrogen peroxide. In general, these conditions are not ideal for immunoassays as they may disrupt receptor-ligand binding and are undesirably complex. The compounds of the present invention have the advantage of not being susceptible to pseudobase formation. Therefore, chemiluminescence may be initiated in one step, by the addition of hydrogen peroxide.

The chemiluminescent compounds of this invention can be stored in a buffer of pH 4–7, preferably degassed, with about 0.1–5% of a cosolvent such as, for example, acetonitrile. The storage temperature should be about 4° C.

The hydrogen peroxide can be provided directly by the addition of hydrogen peroxide. Hydrogen peroxide can also be provided by a hydrogen peroxide producing means. One such means for producing hydrogen peroxide is a compound that produces hydrogen peroxide when added to an aqueous assay medium, for example, perboric acid and acyl peroxides such as dibenzoyl peroxide or metachloroperbenzoic acid. Another means for producing hydrogen peroxide, suitable for use in this invention, is the use of an oxidase and its corresponding substrate, for example, glucose oxidase and glucose. Hydrogen peroxide can also be produced by use of a reducing agent such as dithioerythrane or a hydroquinone and a metal ion such as iron or copper.

Optionally, a catalyst can be added in addition to hydrogen peroxide to enhance chemiluminescence. Suitable catalysts include, by way of illustration and not limitation, perborates, persulfates, per salts of metals in high oxidation states, horseradish peroxidase, hemoglobin, iron phthalocyanine, and potassium ferrocyanide.

One embodiment of the chemiluminescent compounds of this invention is Compound (I) having the formula:

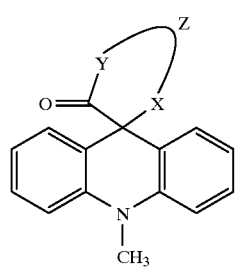

(I)

wherein: X and Y are independently selected from the group consisting of O, S, Se and NH; and Z is a chain, 1–5 atoms in length; where 0 to 8 hydrogens of Compound (I) alone or taken together, may be substituted by a W where each W is independently selected and is comprised of 1–50 atoms, other than hydrogen. One to four of the aromatic carbon atoms of Compound (I) may be replaced by nitrogen atoms. Further, 0 to 1 hydrogen of Compound (I) may be substituted by an organic radical.

Compound (I) can have a variety of such W substituents without departing from the scope of the invention. Selection of the particular substituent groups is only limited by the ability of one skilled in the art to prepare stable compounds that have the chemiluminescent properties of the present invention. Frequently, electron donating substituents will be employed in order to increase reactivity with peroxide. These electron donating groups include, by way of illustration and not limitation, hydroxy, ethers, and amines, in particular dialkyl amines. Where reduction in reactivity is desired, electron withdrawing groups may be employed. These electron withdrawing groups include, by way of illustration and not limitation, aryl; a carbonyl or sulfonyl; a halogen, in particular fluorine and chlorine, and groups such as perfluoroalkyl, polyfluorohydrocarbyl and trichloroethyl; sulfonamide; and carbamate.

Additionally, it may be desirable to attach a fluorescent group that will allow the wavelength of the emitted light to be shifted. In general, the fluorescer should absorb light at wavelengths greater than 400 nm. Useful fluorescers include, by way of illustration and not limitation, coumarins such as umbelliferone; xanthenes such as fluorescein and rhodamine; and squarates. Additionally, groups that accept triplet energy and then emit efficiently, can be used, such as lanthanide chelates, particularly Eu and Sm, and dibromoanthracene.

In a preferred embodiment of Compound (I), X and Y are independently selected from the group consisting of O, S and NH; and Z is a chain, 1–2 atoms in length. Even more preferably, Z is a chain, comprised of two carbon atoms, which atoms are part of a benzene ring, and at least one hydrogen in the benzene ring is substituted by a W. An example of such a compound is Compound (Ia), having the following structure:

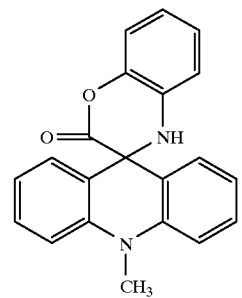

(Ia)

Examples of other compounds within the class described as Compound (I) include the following, by way of illustration and not limitation:

Compound (Ib), having the following structure:

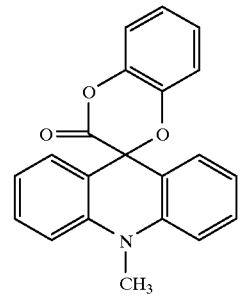

(Ib)

Compound (Ic), having the following structure:

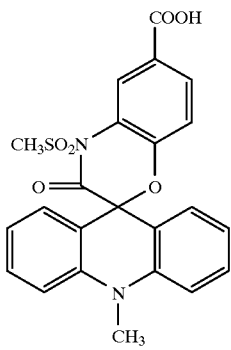
(Ic)

Compound (Id), having the following structure:

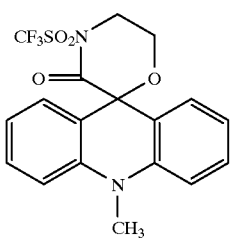
(Id)

Compound (Ie), having the following structure:

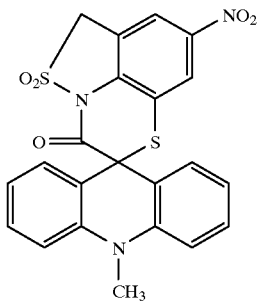
(Ie)

Compound (If), having the following structure:

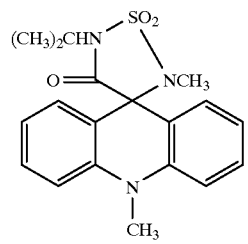
(If)

Another embodiment of the chemiluminescent compounds of this invention is Compound (II) having the formula:

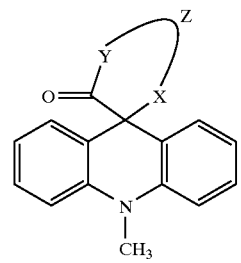
(II)

wherein: X' and Y' are each comprised of a chain of one atom and are independently selected from the group consisting of O, S, Se, NH, NR', $NSO_2R'$ and NCOR', where R' is selected from the group consisting of alkyl, aryl and halogenated alkyl groups; Z is a group linking X' and Y' comprising a chain of 1–2 atoms, where one atom is C and the other atom is selected from the group consisting of C, O, S and N. One or more hydrogens of Compound (II) may be replaced by one or more organic radicals which may be taken together to form rings or double bonds, and one to four of the aromatic carbon atoms may be replaced by nitrogen atoms.

Examples of compounds within the class described as Compound (II) include the following, by way of illustration and not limitation:

Compound (IIa), having the following structure:

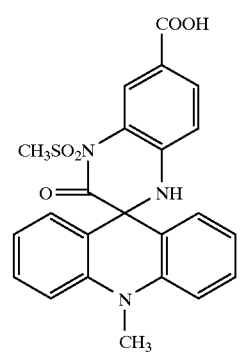
(IIa)

and Compound (IIb), having the following structure:

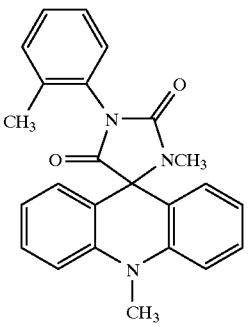
(IIb)

Another embodiment of the chemiluminescent compounds of this invention is Compound (III) having the formula:

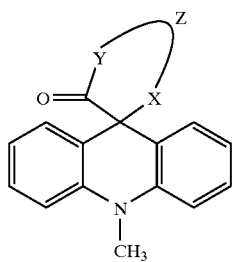

(III)

wherein: X" and Y" are each comprised of a chain of one atom and are independently selected from the group consisting of O, S and N(E)$_p$R", where E is selected from the group consisting of CO and SO$_2$, p is an integer from 0–1, and R" is selected from the group consisting of H, lower alkyls and halogenated lower alkyls; Z" is a group linking X" and Y" comprising a chain of 1–2 atoms, where one atom is C and the other atom is selected from the group consisting of C, O, S and N. One or more hydrogens of Compound (III) may be substituted by organic radicals. The organic radical can be a specific binding pair member, for example a hapten or antibody, or the radical can be a fluorescent group.

An example of a compound within this class is Compound (IIIa), having the following structure:

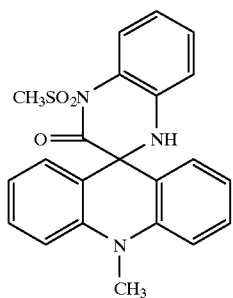

(IIIa)

Another embodiment of the chemiluminescent compounds of this invention is Compound (IV) having the formula:

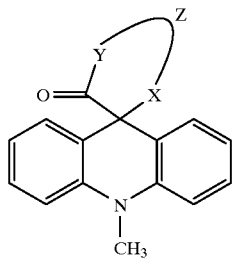

(IV)

wherein: X'" and Y'" are each comprised of one atom and are independently selected from the group consisting of O, S and NH; Z'" is a group linking X'" and Y'" comprising a chain of 1–2 atoms where one atom is C and the other atom is selected from the group consisting of C, O, S and N. One or more hydrogens of Compound (IV) may be substituted by organic radicals.

An example of a compound within this class is Compound (IVa), having the following structure:

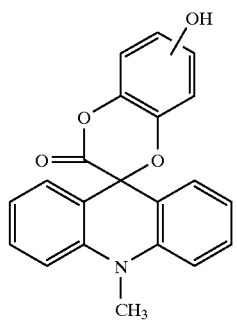

(IVa)

The chemiluminescent compounds of this invention are luminescent at a pH of about 6–10, preferably, 7–9 and can be chemically activated by hydrogen peroxide.

The chemiluminescent compound may contain a group or functionality imparting solubility characteristics. For example, it is possible to incorporate a group or functionality into the compound that will render the compound soluble in water to an extent of at least one nanomolar. The group imparting water solubility generally comprises from 1–30 atoms, preferably 1–12 atoms, other than hydrogen, which atoms are selected from the group consisting of carbon, oxygen, nitrogen, sulfur, phosphorous, and halogen of atomic number 9-53. Such groups or functionalities can include a sulfonate, phosphate, phosphonate, carboxylate, hydroxyl, amine, ether, amide, and the like. It is also possible to incorporate a group or functionality into the compound that will render the compound lipid soluble. The group imparting lipid solubility will usually be comprised of one or more alkyl or aryl groups having at least a total of 7 carbon atoms and preferably at least 12 carbon atoms, and will contain a low ratio of heteroatoms, other than halogen, to carbon, usually 0–10%. Such groups or functionalities can include, by way of illustration and not limitation, a benzyl, dodecyl, eicosyl, dioctyl amino, decyloxy and the like.

The chemiluminescent compounds of this invention may be associated with another compound, such as a specific binding pair (sbp) member, for example, a ligand, hapten, receptor, antibody, or nucleic acid, or a fluorescent molecule. Preferably the chemiluminescent compound is covalently bound to the other compound by a bond or linking group.

Another compound can be bound to any atom but it will frequently be convenient to bind it to the nitrogen on the acridine ring system or to the linking group Z, particularly when the linking group contains an aromatic ring. A wide variety of linking groups may be employed to bond the chemiluminescent compound and the other compound, for example, an sbp member. The choice of linking group will vary widely, depending upon the available functionalities or upon functionalities which may be present or readily introduced into the chemiluminescent compound or sbp member, the desired length of the linking arm, the desirability of having the linking arm provide for a particular environment, chemical property or physical property, e.g. positively or negatively charged, solubility enhancement, dipole effects, or the like. The linking group preferably includes a non-oxo-carbonyl, carbamoyl, thiocarbamoyl, sulfonyl, amino, thio, particularly a functionality having a non-oxo-carbonyl, and sulfur analogs thereof.

A functionality for attachment such as carboxylic acid, hydroxyl, thiol, amino, aldehyde, activated ethylenes such as maleimide, sulfonic acids, and the like can be introduced into the chemiluminescent compound or the sbp member if such functionality is not originally present in the chemiluminescent compound or the sbp member. Methods of conjugation involving sbp members are described in, e.g., U.S. Pat. No. 3,817,837, the relevant disclosure of which is incorporated herein by reference.

The compounds of the present invention can be prepared, for example, by the following reaction sequence, the individual steps of which are separately known in the art. Some of the chemiluminescent compounds of the present invention can conveniently be prepared from the corresponding 9-acridinium carboxylic acid or an activated derivative thereof. The compound can be caused to react with the compound H—Y—Z—X—H, where X, Y and Z are defined as for Compound (I). Similarly, H—Y'—Z'—X'—H, is suitable, and so forth. A polar solvent such as tetrahydrofuran, ethanol, methylene chloride, dimethyl formamide or dimethyl sulfoxide, will usually be employed. Depending upon the specific structure of H—Y—Z—X—H, it may be desirable to employ a non-nucleophilic base such as a tertiary amine, potassium carbonate or a metal hydride. The resulting product can be collected and purified by, for example, recrystallization, sublimation, chromatography, or the like.

One embodiment of the present invention pertains to a chemiluminescent composition comprising a chemiluminescent compound of this invention in a pH 6–10 aqueous solution containing hydrogen peroxide or a means for producing hydrogen peroxide. The chemiluminescent compound can be associated with another molecule such as an sbp member, for example, a hapten or an antibody, in the manner described above. Compound (I) is particularly suited for use in such a composition. If peroxide is to be detected, it will usually be desirable to have a relatively high concentration of the chemiluminescent compound, usually $10^{-6}$ to $10^{-1}$ M, preferably at least $10^{-3}$ M. Where the chemiluminescent compound is used as a label, it will usually be desirable to use high peroxide concentrations, usually $10^{-4}$ to $10^{-1}$ M, preferable at least $10^{-2}$ M.

Another embodiment of the present invention is a light emitting chemical composition comprised of hydrogen peroxide and a chemiluminescent compound of this invention, for example, Compound (II). It is usually desirable to have at least $10^{-4}$ M of the chemiluminescent compound and at least $10^{-3}$ M hydrogen peroxide or a means of producing this concentration of hydrogen peroxide. More preferably, there is at least $10^{-3}$ M of the chemiluminescent compound and at least $10^{-2}$ M of hydrogen peroxide.

Another embodiment of the invention pertain to a compound having the following formula:

where A is a chemiluminescent compound of this invention, for example Compound (III), L is a linking group, and Q is hydrogen or an sbp member.

The method and compositions of the invention may be adapted to most assays involving sbp members such as ligand-receptor, e.g., antigen-antibody reactions, polynucleotide binding assays, and so forth. The assays may be homogeneous or heterogeneous, competitive or sandwich. In a homogeneous assay approach, the sample may be pretreated if necessary to remove unwanted materials. The immunological reaction for a sandwich type assay usually involves an sbp member, e.g., an antibody, that is complementary to the analyte and bound to the chemiluminescent compound, a second sbp member, e.g., antibody, that is also complementary to the analyte, and the sample of interest. In a competitive protocol the chemiluminescent compound may be associated with an sbp member that is analogous to, usually a derivative of, the analyte or with an sbp member complementary to the analyte, e.g., an antibody.

The advantage of using the compounds of this invention in an assay is that the pH of the assay medium does not have to be increased prior to activation, as is the case with other chemiluminescent compounds known in the art.

In a homogeneous assay after all of the reagents have been combined, they can be incubated, if desired. Then, the chemiluminescent compound is activated and the resulting light emitted is measured. The emitted light is related to the amount of the analyte in the sample tested. The amounts of the reagents of the invention employed in a homogeneous assay depend on the nature of the analyte.

In a heterogeneous assay approach, a sample suspected of containing an analyte, which is an sbp member, is combined with a reagent that is comprised of a complementary sbp member bound to a support, which may be a surface or a particle having the chemiluminescent compound. These materials are generally combined either simultaneously or wholly or partially sequentially. The support is then separated from the liquid phase and either the solid phase or the liquid phase is examined for the presence of luminescent energy, usually by providing the a means of providing peroxide.

Several different embodiments of the present invention involve the use of the chemiluminescent compounds in methods for determining analytes. The luminescence or light produced by the chemiluminescent compounds of this invention in the assays described below can be measured visually, photographically, actinometrically, spectrophotometrically or by any other convenient means to determine the amount thereof, which is related to the amount of analyte in the medium. A large variety of commercially available equipment is suitable for chemiluminescence detection including luminometers that are designed for research or clinical applications, fluorometers, instant photographic cameras and filters, and the like. Usually chemiluminescence will be detected instrumentally rather than visually, and will usually be detected by a photomultiplier tube or photodiode rather than actinometrically or photographically.

One such method has the steps of combining a solution of the chemiluminescent solution with a sample having an unknown amount of hydrogen peroxide and detecting the luminescence generated, the amount thereof being related to the amount of hydrogen peroxide in the sample.

Another such method has the following steps: (a) combining in a liquid medium (1) a sample suspected of containing the analyte, (2) a chemiluminescent compound of this invention, for example, Compound (II), and (3) a means for chemically activating the chemiluminescent compound; and (b) detecting the amount of luminescence generated by the compound, the amount thereof being related to the amount of analyte in the sample.

Combining the elements in step (a) can occur simultaneously or sequentially. For example, where the chemically activating means is hydrogen peroxide, in one embodiment, the hydrogen peroxide is combined with the medium simultaneously with the combining of the sample and the chemiluminescent compound. In another embodiment, the hydrogen peroxide is added to the medium after the combining of the sample and the chemiluminescent compound.

Another method involves (1) combining the chemiluminescent compound with a sample containing an analyte that directly or indirectly can produce hydrogen peroxide, (2) adding any ancillary reagents required to produce hydrogen peroxide as a function of the presence of the analyte, and (3)

detecting the luminescence produced by the mixture; where the components may be added in any convenient order.

In another embodiment of the invention, the chemiluminescent compound is attached to a support, preferably a support that does not absorb light at the emission wavelength of the chemiluminescent compound. A sample suspected of containing hydrogen peroxide or an analyte that can affect the formation of hydrogen peroxide, is caused to flow past the support and luminescence produced at the surface of the support is detected. This embodiment is particularly suitable for injection flow analysis and continuous flow analysis.

Another aspect of this invention involves a method for determining an analyte, having the following steps: (a) combining in a medium (1) a sample suspected of containing the analyte and (2) a label reagent comprising a first sbp member associated with a chemiluminescent compound, for example, Compound (III), wherein the first sbp member is capable of binding to the analyte or to a second sbp member capable of binding to the analyte, to form a complex in an amount related to the presence of the analyte; (b) chemically activating the chemiluminescent compound; and (c) detecting the amount of luminescence generated by the chemiluminescent compound, the amount thereof being related to the amount of analyte in the sample.

Conditions are chosen such that in step (a) an sbp member complex is formed in relation to the presence of the analyte. For example, the first sbp member may be capable of binding to the analyte or a second sbp member to form a complex related to the presence of the analyte.

The first sbp member can be covalently bound to the chemiluminescent compound. The analyte and the first sbp member are each independently selected from the group consisting of ligands, receptors, and polynucleotides. The second sbp member can be analogous or complementary to the analyte. In another embodiment, the second sbp member is analogous to or complementary to a third sbp member bound to a support.

The complex formed in step (a) can become bound to a support. In another embodiment, the second or third sbp member is bound to a support.

Another embodiment of a method for determining an analyte in accordance with the present invention, comprises the following steps: (a) combining in an assay medium (1) a sample suspected of containing an analyte and (2) a label reagent comprising a member of a specific binding pair (sbp member) bound to a chemiluminescent compound, for example, Compound (IV), under conditions wherein an sbp member complex involving the label reagent is formed in relation to the presence of analyte in the sample; (b) chemically activating the chemiluminescent compound; and (c) examining the assay medium for a signal, the presence or intensity thereof being related to the amount of analyte in the sample. Chemical activation can be by hydrogen peroxide.

The first sbp member may be analogous or complementary to the analyte. The assay medium may comprise a second sbp member other than the analyte, which may be complementary or analogous to the analyte and/or to the first sbp member. The second sbp member can also be analogous to or complementary to a third sbp member. The analyte and sbp members are each independently selected from the group consisting of ligands, receptors, and polynucleotides.

In this method, the second or third sbp member can be bound to, or capable of becoming bound to, a support. The support can be combined with the assay medium prior to, simultaneously with, or subsequent to the addition of the label reagent.

Another embodiment of a method for determining an analyte has the following steps: (a) combining in an assay medium either wholly or partially sequentially, (1) a sample suspected of containing an analyte, (2) a label reagent comprising a first member of a specific binding pair (sbp member) bound to a chemiluminescent compound, for example, Compound (II), and (3) an insolubilized reagent comprising a second sbp member under conditions wherein an sbp member complex involving the label reagent and the insolubilized reagent is formed in relation to the presence of analyte in the sample; (b) separating the assay medium and the insolubilized reagent; (c) chemically activating the chemiluminescent compound in the medium or on the insolubilized reagent; and (d) examining the assay medium or the reagent for a signal, the presence or intensity thereof being related to the amount of analyte in the sample. Chemical activation may be by hydrogen peroxide.

The analyte and sbp members of this method are each independently selected from the group consisting of ligands, receptors, and polynucleotides. The sbp members can be complementary to the analyte. In one embodiment, the first sbp member is analogous to the analyte and the second sbp member is complementary to the analyte and the first sbp member.

Another aspect of this invention involves an improved assay for an analyte wherein the presence or amount of the analyte is related to the luminescence produced by hydrogen peroxide and a chemiluminescent compound, for example, Compound (III), wherein the improvement comprises producing the luminescence by the reaction of hydrogen peroxide with the chemiluminescent compounds of this invention.

The chemiluminescent compounds of this invention are particularly useful in assays for the detection of oxidase activity or the presence of compounds that serve as substrates for an oxidase. An oxidase, upon reaction with its substrate produces hydrogen peroxide, which chemically activates the chemiluminescent compound. For example, addition of glucose to a medium suspected of containing glucose oxidase or vice versa, results in the production of hydrogen peroxide if the oxidase is present in the medium. When a chemiluminescent compound of this invention is added to the medium, it luminesces when activated by the hydrogen peroxide.

More generally, the chemiluminescent compounds of this invention are useful for the detection of other catalysts or reagents that can produce hydrogen peroxide. For example, iron and copper salts produce hydrogen peroxide in the presence of suitable reducing agents such as mercaptans or hydroquinones. The compounds of this invention combined with all but one of the components required to produce hydrogen peroxide can be combined with the sample suspected of containing the remaining component, the presence of which is determined by detecting the amount of luminescence.

The reactions can be carried out in solution or one or more of the components can be attached to a support. For example, D-amino acids can be detected by attaching D-amino oxidase to a support and a chemiluminescent compound of this invention to a support. A solution sample suspected of containing a D-amino acid will then be contacted with the D-amino acid oxidase on its support and simultaneously or subsequently contacted with the chemiluminescent compound on its support. The medium can be an aqueous buffer suitable to optimize the turnover, the stability of the enzyme, and the reactivity of the chemiluminescent compound with hydrogen peroxide.

If the assay involves an aqueous medium, it may be desirable to have the chemiluminescent compound contain a group or functionality imparting water solubility. This group or functionality can be the sbp member to which the chemiluminescent compound is conjugated, for example, a poly (amino)acid. The group or functionality can also be part of the chemiluminescent compound itself. Water insoluble chemiluminescent compounds can also be employed, for example, when the medium is not water. The compound is attached to a solid support or the water contains a substance that will render the chemiluminescent compound soluble. Such a substance can be, for example, a detergent or a complexing agent such as cyclodextrin.

In one embodiment of the invention, the chemiluminescent compound is bound to an energy acceptor. As used herein, the term "energy acceptor" means a chromophore having substantial absorption higher than 310 nm, normally higher than 350 nm, and preferably higher than about 400 nm. The choice of the energy acceptor is generally governed by the particular chemiluminescent compound used and will usually be capable of absorbing light emitted by the chemiluminescent compound. The energy acceptor may also be included in the assay medium without being bound to the chemiluminescent compound. In this situation, the absorption maximum of the energy acceptor will preferably be at similar wavelength as the emission maximum of the chemiluminescent compound. A high extinction coefficient is desirable, usually in excess of 10, preferably in excess of $10^3$, and particularly preferred in excess of $10^4$. The concentration of the energy acceptor will usually be from $10^{-6}$ to $10^{-1}$ M, preferably $10^{-4}$ to $10^{-1}$ M. Usually, the energy acceptor will fluoresce with high quantum yield, preferably at least 0.1. A number of such fluorescers are described in U.S. Pat. No. 4,174,384 at columns 7 and 8, the relevant portions of which are incorporated herein by reference.

The above-described assays for an analyte will normally be carried out in an aqueous buffered medium at a moderate pH, generally that which provides optimum assay sensitivity. As explained above, the assay can be performed either without separation (homogeneous) or with separation (heterogeneous) of any of the assay components or products.

The aqueous medium may be solely water or may include from 0.01 to 80 or more volume percent of a cosolvent. For aqueous solvents, the pH for the medium will usually be in the range of about 4 to 13, more usually in the range of about 5 to 10, and preferably in the range of about 6.5 to 9.5. The pH will usually be a compromise between optimum binding of the binding members, when binding members are used, the pH optimum for other reagents of the assay such as members of the signal producing system, and the stability of each of the reagents amd the analyte. For example, the activated chemiluminescent compound requires a certain pH range in order to decay to produce luminescence, within the range of pH 6–10, preferably 7–9.

In aqueous media, various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. When a non-aqueous medium is used, it will usually comprise a polar solvent such as alcohols, ethers, esters, haloalkanes, sulfoxides, amides, and the like.

Moderate temperatures are normally employed for carrying out the assay and usually constant temperature, preferably, room temperature, during the period of the measurement. Incubation temperatures will normally range from about 5° to 99° C., usually from about 15° to 70° C., more usually 20 to 45° C. Temperatures during measurements will generally range from about 10° to 70° C., more usually from about 20° to 45° C., more usually 20° to 25° C.

The concentration of analyte which may be assayed will generally vary from about $10^{-5}$ to $10^{-20}$ M, more usually from about $10^{-6}$ to $10^{-14}$ M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

While the order of addition may be varied widely, there will be certain preferences depending on the nature of the assay. The simplest order of addition particularly for a homogeneous assay is to add all the materials simultaneously. Alternatively, the reagents can be combined wholly or partially sequentially. Optionally, an incubation step may be involved after the reagents are combined, generally ranging from about 30 seconds to 6 hours, more usually from about 2 minutes to 1 hour.

When the chemiluminescent compound is caused to become associated with the surface as the result of the presence of analyte, it will usually be associated with an sbp member. This may be accomplished in a number of ways. The chemiluminescent compound may contain a functionality for attachment to an sbp member or the sbp member may contain the functionality for attaching to the chemiluminescent compound. The attachment may be accomplished by a direct bond between the two molecules or a linking group can be employed between the sbp member and the chemiluminescent compound. In another embodiment the chemiluminescent compound can be bound to or incorporated in a particle, to which is also attached an sbp member. In both cases the sbp member is capable of binding to the analyte. The chemiluminescent compound can be incorporated into the particle by virtue of being soluble in at least one phase of the particle. The chemiluminescent compound may be bound to the particle when it is not incorporated into the particle. For this purpose the chemiluminescent compound or the particle, or component thereof, is functionalized to provide a means of attaching the chemiluminescent compound and the particle. For particles that are oil droplets or lipid bilayers, the chemiluminescent compound can be bound to the particle by attachment to a long hydrocarbon chain that is compatible with the particle composition. Frequently, at least one, and preferably two, hydrocarbon chains are employed having 8 to 20 or more carbon atoms.

As mentioned above, the chemiluminescent compound may be "associated with an sbp member", and thus one use of a compound of the present invention is as a label. As used herein, the term "associated with an sbp member" includes the following. Usually, the association of the chemiluminescent compound and sbp member is through covalent binding. However, the label reagent can further comprise a suspendible particle to which the chemiluminescent compound is bound or in which the chemiluminescent compound is non-covalently incorporated. The suspendible particle will also have the sbp member bound to it. This sbp member is generally capable of binding to the analyte or to an sbp member capable of binding to the analyte. The sbp member bound to the chemiluminescent compound can also be analogous to the analyte, in which case a competitive assay protocol can result.

As can be seen, the assays of this invention provide for convenient methods for detecting and measuring a wide variety of analytes in a simple, efficient, reproducible manner, which can employ visual inspection or conventional equipment for measuring the amount of light produced during the reaction.

The following assays are provided by way of illustration and not limitation to enable one skilled in the art to appreciate the scope of the present invention and to practice the invention without undue experimentation. It will be appreciated that the choice of analytes, chemiluminescent compounds, surfaces, particles and reaction conditions will be suggested to those skilled in the art in view of the disclosure herein and the examples that follow.

In the following assays, components are combined in a predominantly aqueous medium of pH 6 to 10.

(A) In an assay for hCG, a chemiluminescent compound of this invention, for example Compound (IIa), conjugated to an antibody to hCG is utilized.

A urine sample is combined with the anti-hCG-chemiluminescent compound conjugate:

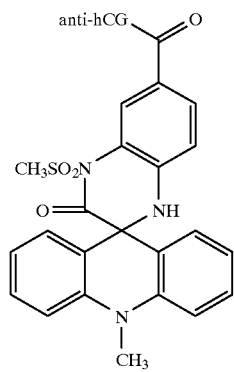

and an antibody against a separate non-overlapping epitope of hCG bound to bound to 1 micron latex particles. After incubation of the suspension for 30 minutes, the particles are separated from the medium by centrifugation, washed and suspended in an aqueous solution containing hydrogen peroxide buffered to pH 8. The intensity of light emitted during the reaction of the chemiluminescent compound and hydrogen peroxide is directly related to the amount of hCG in the sample.

(B) In an assay for digoxin in serum, a chemiluminescent compound of this invention, for example Compound (IIIa), conjugated to digoxigenin is utilized. The digoxigenin-chemiluminescent compound conjugate:

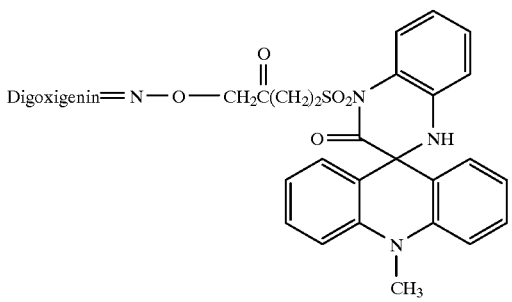

is incubated with the sample in a polystyrene well whose surface is coated with an antibody to digoxin. After incubation for 10 minutes, the polystyrene well is washed and hydrogen peroxide at pH 9 is added. The intensity of the light emitted following addition of hydrogen peroxide is inversely related to the concentration of digoxin in the sample.

(C) In an assay for albumin in urine, a chemiluminescent compound of this invention, for example Compound (Ic), conjugated to an antibody to albumin is utilized. The sample is combined with the anti-albumin-chemiluminescent compound conjugate:

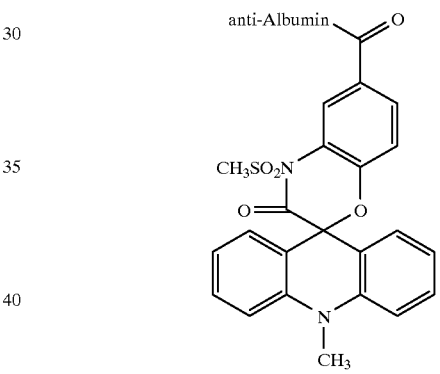

and an antibody to albumin directed against a non-overlapping albumin epitope that is bound to glass beads. The medium is incubated for 10 minutes and the beads separated and washed. The beads are then placed in an aqueous medium to which hydrogen peroxide is added. The intensity of the light emitted is directly related to the amount of albumin in the sample.

(D) In an assay for a target polynucleotide sequence in a sample containing DNA, the 3' end of a first 25-base oligonucleotide complementary with the target sequence is conjugated to a chemiluminescent compound of this invention, for example, Compound (Ib):

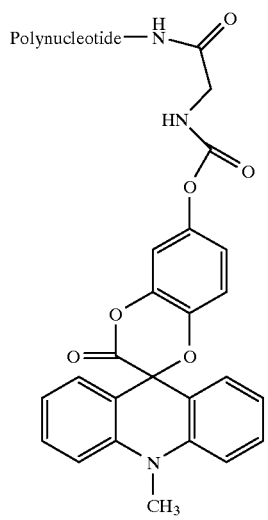

The 5' end of a second 25-base oligonucleotide complementary to the target sequence at a site contiguous with and 5' to the site of binding of the first oligonucleotide, is conjugated with fluorescein. The two oligonucleotides are mixed with the sample. The medium is then heated to 75° C. and cooled to 55° C. to permit hybridization of the oligonucleotides to any target sequence present. Hydrogen peroxide is added following completion of the hybridization reaction. The light emitted at 520 nm is measured by use of a suitable band pass filter. The light intensity at this wavelength is directly related to the presence of the target sequence.

(E) In an assay for hepatitis B surface antigen (HBsAg) in serum, the sample is combined with antibodies to HBsAg bound to a chemiluminescent compound of this invention in a tube coated with antibodies to the HBsAg antigen. After incubation of the mixture for one hour, the tubes are washed and hydrogen peroxide is added. The emitted light intensity is related to the amount of HBsAg in the sample.

(F) In an assay for glucose oxidase, the sample is combined in a pH 8 buffer with glucose and a chemiluminescent compound of this invention. The intensity of the emitted light is indicative of the amount of glucose oxidase present in the sample.

Another aspect of the present invention relates to kits useful for conveniently performing the assay method of the invention for determining the presence or amount of an analyte in a sample suspected of containing the analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents.

One such kit comprises in packaged combination (1) a composition comprising a chemiluminescent compound of this invention, for example Compound (I), having bound thereto a specific binding pair member and (2) hydrogen peroxide or a means for producing hydrogen peroxide. Another kit encompassed by this invention is useful for the detection of hydrogen peroxide or an analyte that modulates the formation of hydrogen peroxide, and comprises in packaged combination (1) a composition comprising the compound A—L—Q described herein and (2) any ancillary reagents required to produce hydrogen peroxide from said analyte when said analyte is not hydrogen peroxide.

Another kit useful for the analysis of a compound capable of producing hydrogen peroxide comprises a chemiluminescent compound of this invention and a catalyst capable of forming hydrogen peroxide from the compound being analyzed.

Another kit useful for detecting hydrogen peroxide or a compound capable of modulating the formation of hydrogen peroxide, comprises a chemiluminescent compound of this invention bound to a solid support.

The kits can also include one or more additional sbp member reagents. An energy acceptor can be attached to an sbp member or a chemiluminescent compound to form a reagent or it can be provided by itself as a reagent. An sbp member that is bound to a surface can also be included. The kits can further include other separately packaged reagents for conducting an assay including ancillary reagents, and so forth. The sbp member(s) of the kit may be selected from the group consisting of ligands, receptors and polynucleotides.

The following examples are offered by way of illustration and not by way of limitation.

EXPERIMENTAL

All temperatures not otherwise indicated are in centigrade. All percents and parts not otherwise indicated are by weight, except for mixtures of liquids which are by volume.

MATERIALS

Ether and tetrahydrofuran (THF) were distilled from sodium/benzophenone ketyl under argon. Pyridine and N,N-dimethyl-formamide (DMF) were dried and distilled from $CaH_2$ prior to use. Anhydrous $CH_3CN$ was purchased from Aldrich. Toluene was dried and distilled from sodium. Hydrogen peroxide was purchased as a 30% solution from Mallinckrodt. All other compounds were either purchased commercially or synthesized as described in the examples. Unless mentioned otherwise, all other solvents were used without further purification, and most reaction were carried out under argon. Silica gel used for flash chromatography was 230–400 mesh ASTM, purchased from Scientific Products while preparative plates (1000 μ) and analytical plates were purchased from Analtech.

$^1$H-NMR was recorded on a FT-IBM WP-100 MHz NMR Spectrometer and a Bruker WP-300 MHz NMR Spectrometer. All chemical shifts were reported in δ units, downfield of TMS. Splitting patterns are designated as follows: s, singlet; d, doublet; t, triplet; q, quartet; m, multiplet; and b, broad.

Infrared spectra were recorded on a Perkin Elmer 297 IR Spectrometer. The abbreviations, s, m, and b, refer to sharp, medium, and broad, respectively.

Desorption chemical ionization (CI) and electron ionization (EI) were done on a Varian-MAT 311A, double focussing high resolution mass spectrometer. A Finnigan TSQ-70 or MAT-8230 were used for fast atom bombardment mass spectra.

UV-Visible absorption spectra and kinetic studies involving time trace were done on an HP 8452A diode array spectrophotometer.

Chemiluminescence measurements were done on an Optocomp I and Turner TD-20e luminometers.

EXAMPLE 1

Synthesis of Chemiluminescent Compound (Ia)

1. Synthesis of N-methylacridinium 9-carbonyl(p-nitrophenylate) ester (2).

N-methylacridinium 9-carbonyl(p-nitrophenylate) ester (2) was prepared in three steps from commercially available acridine 9-carboxylic acid (1), by the method described in McCapra, et al. *Pure and Applied Chemistry* 24:611 (1970).

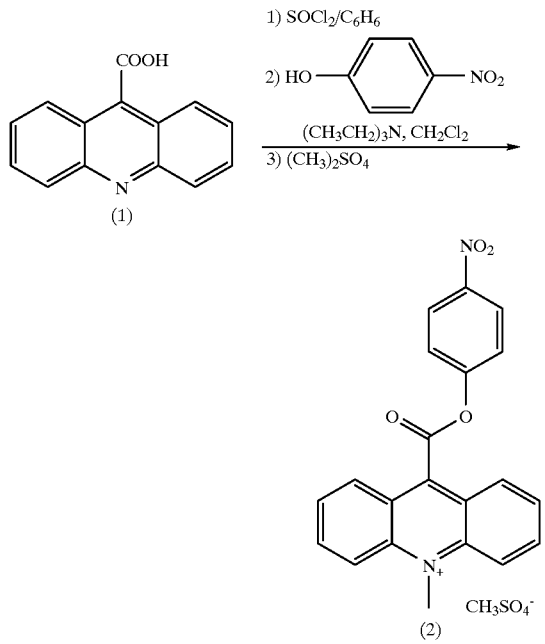

2. Synthesis of the spiro-acridan (Ia).

To a dried argon-purged 20 mL round-bottom flask containing dry acetonitrile (5.0 mL) at room temperature, were added the ester (2) (233 mg, 0.5 mmol) and o-aminophenol (220 mg, 4.0 mmol).

The reaction mixture was heated to 70° C. with gentle stirring for 24 hours under argon. The solvent was evaporated under vacuum to obtain a yellow oil, which was purified on preparative thin layer chromatography (TLC) (silica gel, 1000 microns) using 20% ethyl acetate in methylene chloride as eluant to obtain 98 mg (60%) of Compound (Ia) as the pure product.

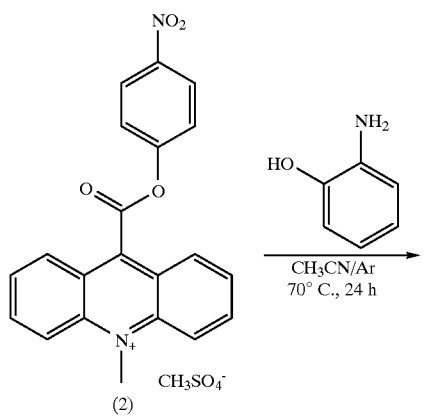

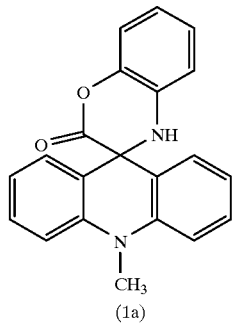

$^1$H-NMR: (CDCl$_3$, 300 MHz): δ3.5(s,3H), 4.5(bs,NH), 6.7–7.5(m,12H)

IR (CHCl$_3$), cm$^{-1}$: 3250(w), 1750(s), 1590(s), 1490(s), 1470(s)

Absorption Spectrum: (0.8 mL borate buffer, pH 9.0+0.2 mL CH$_3$CN) 265 nm (ε~20,000) (0.8 mL dilute HCl, pH 1.1+0.2 mL CH$_3$CN) 357 nm (ε 15,600), 425 nm (ε 4000)

Mass Spectrum (CI): m/e 328(M$^+$)

High Resolution Mass Spectrum: Empirical Formula: C$_{21}$H$_{16}$N$_2$O$_2$ Theoretical Mass: 328.121178 Measured Mass: 328.120892

EXAMPLE 2

Synthesis of Chemiluminescent Compound (IVa)

10-Methylacridinium-9-carboxylate (3) was prepared by the method described in McCapra, et al. *Pure and Applied Chemistry* 24:611 (1970).

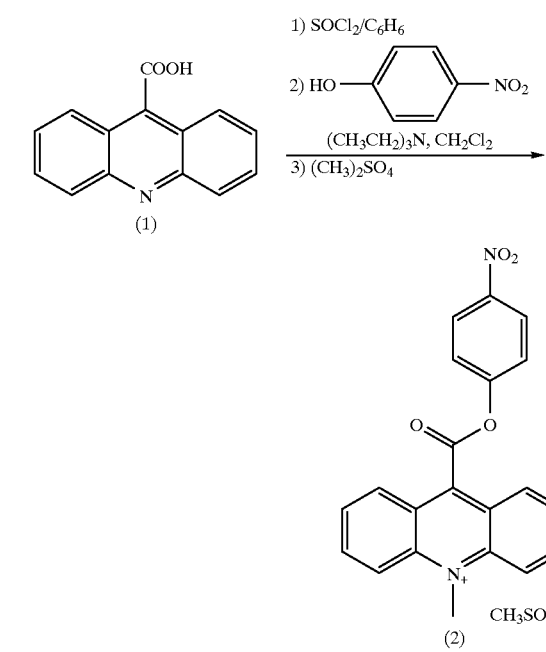

To a dry 20 mL round-bottom flask containing 5.0 mL of DMF, were added the carboxylate (3) (274 mg, 1.0 mmol) and carbonyl diimidazole (CDI) (225 mg, 1.5 mmol). The reaction mixture was stirred at room temperature for 16 hours. At this point, an aliquot of reaction mixture was found to be highly chemiluminescent when perborate (pH 9.5) was added. 1,2,4-Trihydroxybenzene (504 mg, 4.0 mmol) in 3 mL of acetonitrile was added to the above reaction mixture. The reaction was allowed to sit under argon for 12 hours.

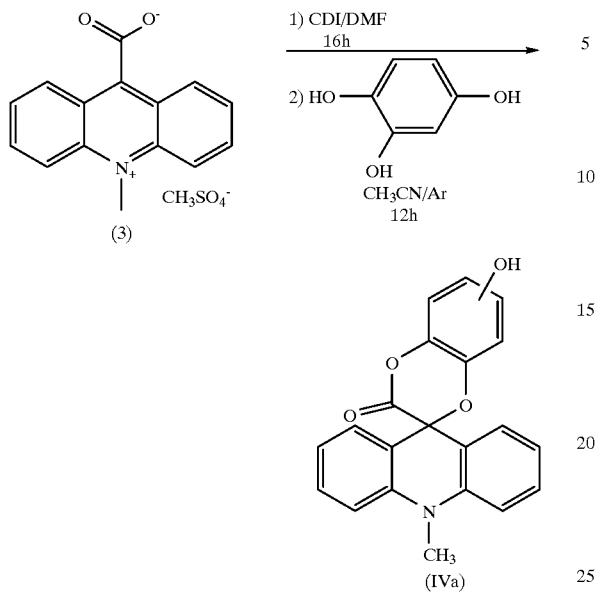

The solvent was evaporated under vacuum to obtain a yellow oil, which was purified on preparative TLC (silica gel, 1000 microns) using 20% acetonitrile in chloroform to obtain 152 mg (44%) of Compound (IVa) as the pure product.

$^1$H-NMR: (CDCl$_3$, 100 MHz): 67 3.55(s,3H), 6.65–7.5 (m,11H)

IR (Neat), cm$^{-1}$: 3450(m), 1750(s), 1590(s), 1460(s)

Mass Spectrum (CI): m/e 345(M$^+$)

EXAMPLE 3

Synthesis of Chemiluminescent Compound (IIIa)

1. Synthesis of 2-amino methylsulfonanilide (5).

A solution of o-phenylene diamine (4) (5.20 g, 48.1 mmol) in CH$_2$Cl$_2$ (100 mL) was treated with methane sulfonyl chloride (3.6 mL, 46.5 mmol) and the mixture stirred until TLC indicated absence of starting material. The mixture was concentrated, adsorbed on alumina and chromatographed with a gradient of CH$_3$OH (0–5%) in CH$_2$Cl$_2$ as the eluant.

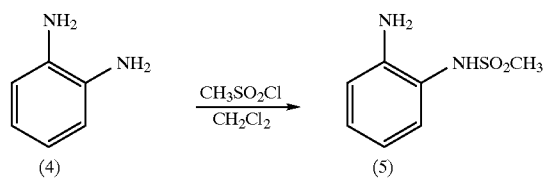

The product (R$_f$=0.6, 1% CH$_3$OH in CH$_2$Cl$_2$, alumina) obtained as a tan colored solid, was crystallized from aqueous CH$_3$CH$_2$OH to yield 6.0 g (67%) of compound (5) as light tan leaflets.

$^1$H-NMR: (CDCl$_3$, 100 MHz): δ7.20(m,2H), 6.86(m,2H), 6.2(b,1H).

2. Synthesis of the spiro-acridan (IIIa).

A suspension of the ester (2) (80 mg, 0.22 mmol) in dry, degassed CH$_3$CN (10 mL), under argon, was treated with the sulfonanilide (5) (40 mg, 0.22 mmol) followed by a drop of (CH$_3$CH$_2$)$_3$N.

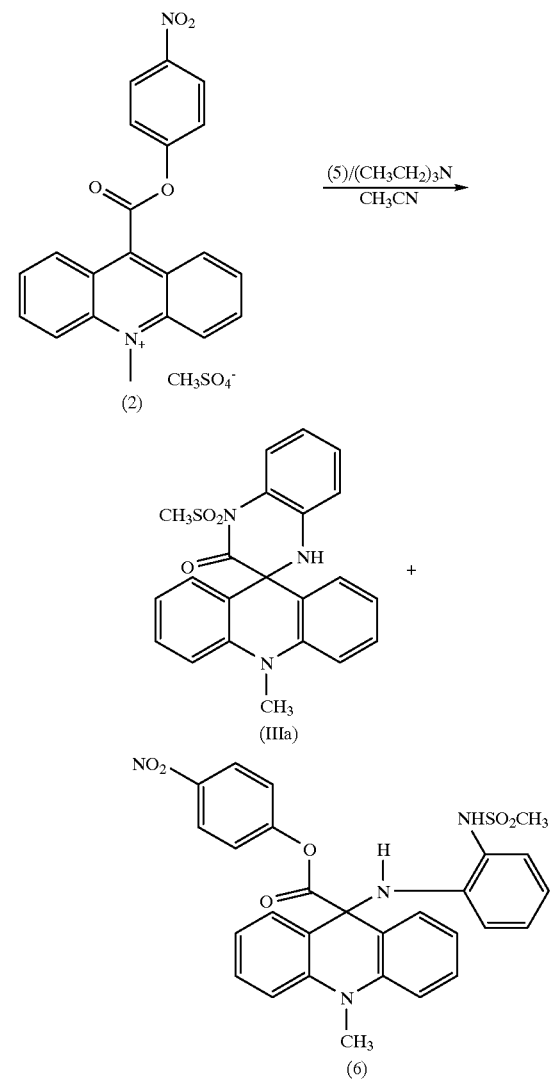

The initial yellow solution, which rapidly turned almost colorless, was stirred for 14 hours. The mixture was concentrated and purified by preparative TLC (silica, CH$_2$Cl$_2$ eluant) to yield 52 mg (60%) of the Compound (IIIa) together with 10 mg (9%) of the 9-adduct (6). The 9-adduct was readily converted to the Compound (IIIa) with NaH in THF.

$^1$H-NMR: (CDCl$_3$, 100 MHz): 67 7.4–6.5(m,12H), 4.40 (s,1H), 3.55(s,3H), 3.50(s,3H)

Mass Spectrum (EI) calc. for C$_{22}$H$_{19}$N$_3$O$_3$S$_1$: 405 found 405 (M$^+$, 10%), 326 (M—SO$_2$CH$_3$, 100%)

UV-Vis (CH$_3$CN), 284 nm (ε=20,000), 328(ε=8,000)

EXAMPLE 4

Synthesis of Chemiluminescent Compound (IIa)

1. Synthesis of 2-amino-5-carboxy methylsulfonanilide (8).

A solution of diaminobenzoic acid (7) (5.0 g, 32.8 mmol) in dry pyridine (100 mL) was stirred and cooled to 0° C. Methane sulfonyl chloride (2.5 mL, 32.3 mmol) was added dropwise over a period of 30 minutes. The reddish color solution was allowed to attain room temperature overnight.

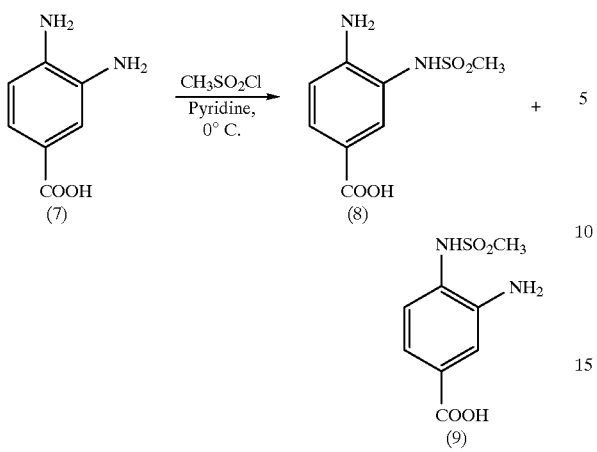

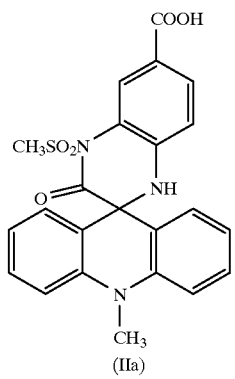

The solution was concentrated to a paste, washed with CH₂Cl₂ (2×100 mL) and filtered. The residue was subsequently washed with cold water and dried in a vacuum oven at 50° C. The ¹H-NMR showed the crude to be a 4:1 (compound (8): compound (9)) mixture of isomers. Crystallization from boiling water afforded 4.10 g (56%) of the sulfonanilide (8) as tan flakes.

¹H-NMR: (DMSO-d₆, 300 MHz): δ8.79(s,1H), 7.67(d, J=1.5 Hz, 1H), 7.56(dd, J=7 Hz, 1.5 Hz, 1H), 6.72(d, J=7 Hz, 1H), 2.95(s,3H)

IR (KBR): 3600(b), 3265(s), 1700(s), 1642(s), 1582(m), 1523(m), 1387(m), 1203(m), 1166(s), 1134(s), 1032(s), 993 (s), 783(s)

Mass Spectrum (EI) calc. for $C_8H_{10}N_2O_4S_1$, 230 found 230 (M⁺, 30%), 151 (M—SO₂CH₃, 100%)

2. Synthesis of the spiro-acridan (IIa).

To a suspension of the ester (2) (200 mg, 0.43 mmol) in anhydrous CH₃CN (25 mL), under argon, was added (CH₃CH₂)₃N (0.5 mL) followed by the sulfonanilide (8) (120 mg, 0.45 mmol). The initial yellow solution gradually turned almost clear, indicating adduct formation. The reaction mixture was concentrated after TLC indicated absence of starting materials.

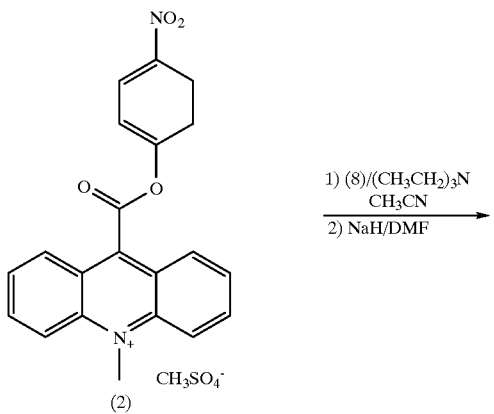

The concentrate was passed through silica (100 g, 10% CH₃CN in CH₂Cl₂) and the higher R_f (0.60–0.40) material, which was a mixture of two compounds, was collected. The mixture (260 mg) was dissolved in anhydrous DMF (20 mL) and treated with NaH (100 mg), batch-wise, allowing the initial effervescence to subside before subsequent additions. After 3 hours, the reaction mixture was quenched with 10% aqueous NH₄Cl (2 mL) and extracted with CH₂Cl₂ (3×50 mL). The aqueous portion was concentrated to 10 mL and acidified to pH 3.0 with 3N HCl, and re-extracted with CH₂Cl₂ (2×25 mL). The combined organic portions were dried over anhydrous Na₂SO₄ and purified by preparative TLC (silica, 10% CH₃OH in CH₂Cl₂) to yield 32 mg (16%) of the spiro-acridan (IIa).

¹H-NMR: (CD₃OD, 300 MHz): δ8.19(s,₁H), 7.74(d, J=8 Hz, 1H), 7.36(m,4H), 7.14(d, J=7.6 Hz, 2H), 6.88(m,3H), 3.59(s,3H), 3.52(s,3H)

Mass Spectrum (CI, CH₄) calc. for $C_{23}H_{19}N_3O_5S_1$: 449 found 449 (M⁺, 22%), 370 (M⁺—SO₂CH₃, 100%)

UV-Vis (CH₃CN): 264 nm (ε=20,000), 326 (ε=7,800)

EXAMPLE 5

Synthesis of Chemiluminescent Compound (Ic)

1. Synthesis of 2-hydroxy-5-carboxy methylsulfonanilide (11)

A solution of the carboxylic acid (10) (3.1 g, 20.2 mmol) in dry pyridine (50 mL) was cooled to 0° C. Methane sulfonyl chloride (1.8 mL), 19.0 mmol) was slowly added over a period of ten minutes. The mixture was stirred for 6 hours and allowed to attain room temperature over this period. The pyridine was distilled off after TLC indicated the absence of any starting material.

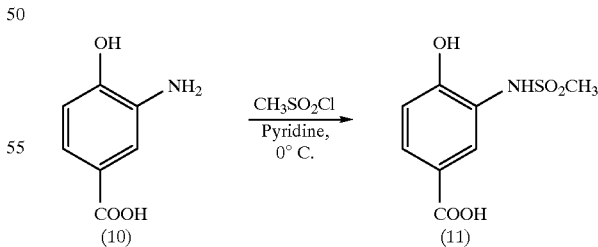

The crude thus obtained was washed with cold water (2×50 mL) and filtered. The residue was crystallized from boiling water to yield 3.3 g (70%) of compound (11) as an off-white solid.

¹H-NMR: (DMSO-d₆, 300 MHz): δ10.7(bs,~1H), 8.87(s, 1H), 7.81(d, J=2 Hz, 1H), 7.66(dd, J=9 and 2 Hz,1H), 6.97(d, J=9 Hz, 1H), 2.96(s,3H).

37

Mass Spectrum (CI, CH$_4$) calc. for C$_8$H$_9$N$_1$O$_5$S$_1$: 231 found 231 (M$^+$, 30%), 152 (M$^+$—SO$_2$CH$_3$, 100%)

2. Synthesis of the spiro-acridan (Ic).

The spiro-acridan (Ic) was prepared by a similar procedure as that used for the spiro-acridan (IIa) in Example 4.

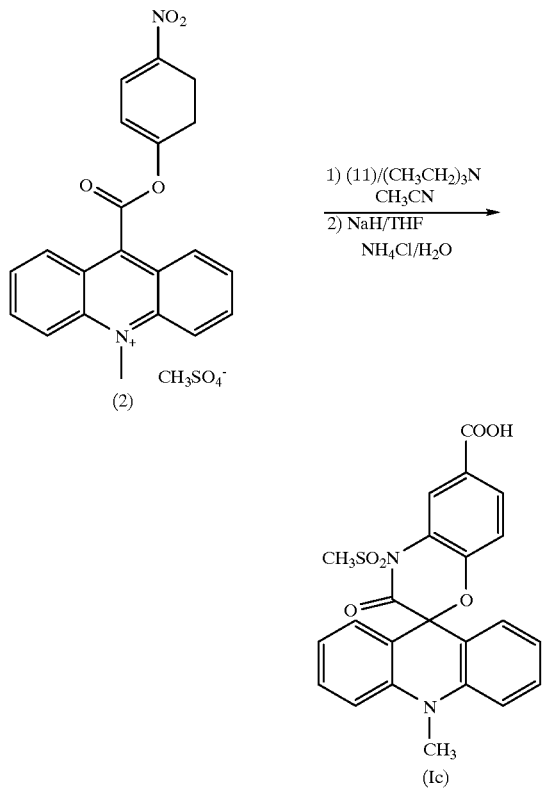

$^1$H-NMR: (CD$_3$OD, 300 MHz): δ8.20(s,1H), 7.74(d, J=8 Hz, 1H), 7.40(m,4H), 7.14(d, J=8 Hz, 2H), 6.94(m,3H), 3.65(m,6H).

EXAMPLE 6

Chemiluminescence Measurements

The acridinium phenyl ester (12) was prepared by the method described in Rauhut, et al., *Journal of Organic Chemistry* 30:3587 (1965).

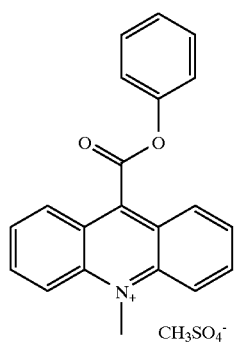

(12)

It was characterized by $^1$H-NMR and mass spectrography. Its absorption spectra in strong acid had a maximum at 368 nm (ε=19,800), consistent with an acridinium nucleus.

38

The chemiluminescent Compound (Ia) was prepared as in Example 1.

TABLE 1

| | Relative Light Units emitted at: | |
|---|---|---|
| Compound | 1.0 pM | 2.0 pM |
| (Ia) | 13.10 | 20.6 |
| | 12.60 | |
| (12) | 1.98 | |

Chemiluminescence for Compound (Ia) was initiated by the addition of 100 mM H$_2$O$_2$ to a borate buffer (pH 9.0, 0.2M) solution of Compound (Ia). Chemiluminescence for compound (12) was initiated by the addition of 1.0 M NaOH to a dilute nitric acid solution of compound (12) containing 10 mM of H$_2$O$_2$. The conditions at which compound (12) was tested were those reported as being the best conditions to obtain maximum chemiluminescence, in Weeks, et al., *Clinical Chemistry* 29:1474–1479 (1983) (the "pH jump method"). Chemiluminescence for both compounds was measured with a Turner luminometer.

EXAMPLE 7

Detectibility of Chemiluminescent Compounds

The detectibility measurements for compounds (Ic), (IIa) and (IIIa) were performed in an Optocomp 1 luminometer equipped with two injectors. Stock solutions of each compound tested were prepared in CH$_3$CN. Serial dilutions were done with a borate buffer (pH 9.0, 200 mM).

100 μL of 10$^{-13}$ M concentration stock solution was further treated with 900 μL of borate buffer in a 12×75 test tube. The test tube was placed in the luminometer and the reaction initiated by the addition of 100 mL of 1% H$_2$O$_2$ in pH 9.0 buffer. The light output was measured with no delay, in a kinetic mode with 10s integrations at 0s intervals. The data is presented in FIGS. 1–3.

EXAMPLE 8

Hydrolytic and Detectibility Testing

The stability and detectibility of chemiluminescent compounds (Ic), (IIa) and (IIIa) were compared with the known compound (12). Compounds (Ic), (IIa) and (IIIa) were chemiluminescent and more stable. In particular, Compounds (IIa) and (IIIa) showed remarkable hydrolytic stability and were detectible at 1.5±0.5×10$^{-14}$ M (15±5 attomoles/mL) when treated with H$_2$O$_2$ at pH 9.0. The signal from all the chemiluminescent compounds was short lived.

TABLE 2

| Compound | Stability at pH 9.0 | Detectibility (mL) pH 9.0 and H$_2$O$_2$ |
|---|---|---|
| (IIIa) | t½ = 12 hours | 10 attomoles |
| (12) | t½ = 290 minutes | 10 attomoles* |
| (IIa) | stable | 10–20 attomoles |
| (Ic) | t½ = 5.3 hours** | 10 attomoles |

*Measured by the pH jump method, acidified sample is treated with H$_2$O$_2$ followed by 1N NaOH (final pH is 13–14)
**Regioisomer may be present

EXAMPLE 9

HRP Enhanced Chemiluminescence

The effect of adding an oxidizing agent, horseradish peroxidase (HRP), to enhance chemiluminescence was studied with Compound (IVa), prepared as in Example 2. The stock solutions used were:

Buffer: borate, pH 8.0 (0.1 M) $H_2O_2$: 1.0 M-deionized water HRP: 1.0 mM/borate buffer, pH 8.0

15 µL of Compound (IVa) (1000 µM) was diluted into 975 µL of borate buffer and 10 µL of $H_2O_2$ was added. The test tube was transferred into a Turner luminometer and the light output monitored. The luminescence signal was 1200 Relative Light Units (RLUS) in the first 10 seconds. The data is presented in FIG. 4.

15 µL of Compound (IVa) (1000 µM) was diluted into 875 µL of borate buffer and 100 mL of HRP. 10 µL of $H_2O_2$ was then added. The test tube was transferred into a Turner luminometer and the light output monitored. The luminescence signal was 3500 RLUs in the first 10 seconds. The data is presented in FIG. 4.

5 µL of Compound (IVa) (1000 µM) was diluted into 885 µL of borate buffer and 100 µL of HRP (1.0 µM). 10 µL of $H_2O_2$ was then added. The test tube was transferred into a Turner luminometer and the light output monitored. The luminescence signal was 1330 RLUs in the first 10 seconds. The data is presented in FIG. 5.

5 µL of compound (2) (1.0 µM) was diluted into 985 µL of borate buffer and 10 µL of $H_2O_2$ was added. The test tube was transferred into a Turner luminometer and the light output monitored. The luminescence signal was 1070 RLUs in the first 10 seconds. The data is presented in FIG. 5.

EXAMPLE 10

Detection of Hydrogen Peroxide

On treatment with glucose oxidase, glucose is transformed into gluconic acid (via gluconolactone) and $H_2O_2$:

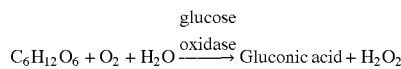

$$C_6H_{12}O_6 + O_2 + H_2O \xrightarrow{\text{glucose oxidase}} \text{Gluconic acid} + H_2O_2$$

Known amounts of $H_2O_2$ in solution were treated with $10^{-6}$ M of Compound (Ia) and the chemiluminescence measured. The minimum amount of $H_2O_2$ that generated light above the background, i.e., signal due to Compound (Ia) in the absence of $H_2O_2$, was $1 \times 10^{-8}$ M. The detectibility limit of $H_2O_2$ by acridinium esters such as compound (12) was found to be $7 \times 10^{-8}$ M.

Although the foregoing invention has been described in some detail by way of illustration-and example for purposes of clarity and understanding, it will be obvious that certain changes or modifications may be practiced within the scope of the appended claims.

What is claimed is:

1. A compound of the formula:

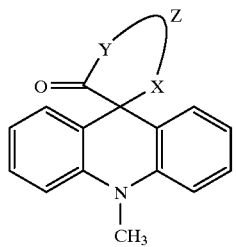

wherein: X is O or S and Y is N, Z is a chain 2 carbon atoms in length, said chain being part of a fused benzene ring; wherein 0 to 8 hydrogens of said compound may be replaced by a W where each W is independently alkyl alkylidine, aryl, aralkyl, or an alkyl, aryl, or aralkyl substituted with one or more radicals of functional groups, wherein the functional groups are independently selected from the group consisting of carboxylic acids, alcohols, thiols, carboxamides, carbamates, carboxylic acid esters, phosphoramides, sulfonamides, ethers, sulfides thioethers, olefins, acetylenes, amines, ketones, aldehydes, nitriles and halogens.

2. The compound of claim 1 having the formula:

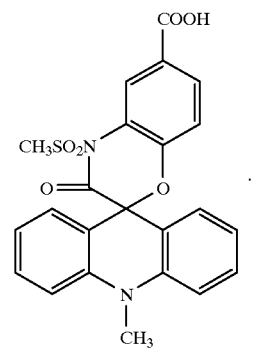

3. The compound of claim 1 wherein: X is O.

4. The compound of Clam 1 wherein at least one hydrogen in said benzene ring is substituted by a W.

5. A chemiluminescent composition comprised of the compound of claim 1 in a pH 6–10 aqueous solution containing hydrogen peroxide.

6. A light emitting chemical composition comprising hydrogen peroxide and a compound having the following formula:

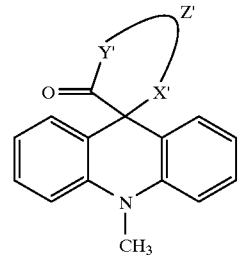

wherein: X' is O or S and Y' is N wherein N is part of a functionality selected from the group consisting of NH, NR', $NSO_2R'$ and NCOR', where R' is selected from the group consisting of alkyl, aryl and halogenated alkyl groups; Z' is a group linking X' and Y' and is a chain of 2 carbon atoms in length, said chain being part of a fused benzene ring; where one or more hydrogens of said compound may be replaced by a W wherein each W is independently alkyl, alkylidine, aryl, aralkyl, or an alkyl, aryl, or aralkyl substituted with one or more radicals of functional groups, wherein the functional groups are independently selected from the group consisting of carboxylic acids, alcohols, thiols, carboxamides, carbamates, carboxylic acid esters, phosphoramides, sulfonamides, ethers, sulfides thioethers, olefins, acetylenes, amines, ketones, aldehydes, nitrites and halogens.

7. The composition of claim 6 which further comprises a catalyst.

8. A compound of the formula:

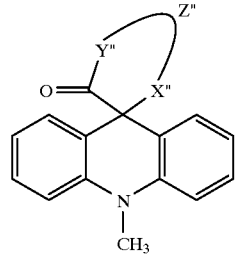

(III)

wherein: X" is O or S and Y" is N (E)$_p$R", where E is selected from the group consisting of CO and SO$_2$, p is an integer from 0–1, and R" is selected from the group consisting of H, lower alkyls and halogenated lower alkyls; Z" is a group linking X" and Y" and is a chain 2 carbon atoms in length, said chain being part of a fused benzene ring; and where one or more hydrogens of said compound may be replaced by a W wherein each W is independently alkyl, alkylidine, aryl, aralkyl, or an alkyl, aryl, or aralkyl substituted with one or more radicals of functional groups, wherein the functional groups are independently selected from the group consisting of carboxylic acids, alcohols, thiols, carboxamides, carbamates, carboxylic acid esters, phosphoramides, sulfonamides, ethers, sulfides thioethers, olefins, acetylenes, amines, ketones, aldehydes, nitrites and halogens.

9. The compound of claim 8 wherein said organic radical is an sbp member.

10. A compound having the following formula:

A—L—Q wherein: A is a compound of the formula:

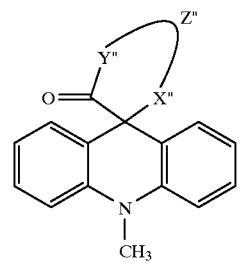

(III)

wherein: X" is O or S and Y" is N (E)$_p$R", where E is selected from the group consisting of CO and SO$_2$, p is an integer from 0–1, and R" is selected from the group consisting of H, lower alkyls and halogenated lower alkyls; Z" is a group linking X" and Y" and is a chain 2 carbon atoms in length, said chain being part of a fused benzene ring; and where one or more hydrogens of said compound may be substituted by a W wherein each W is independently alkyl, alkylidine, aryl, aralkyl, or an alkyl, aryl, or aralkyl substituted with one or more radicals of functional groups, wherein the functional groups are independently selected from the group consisting of carboxylic acids, alcohols, thiols, carboxamides, carbamates, carboxylic acid esters, phosphoramides, sulfonamides, ethers, sulfides thioethers, olefins, acetylenes. amines, ketones, aldehydes, nitriles and halogens; L is a linking group; and Q is hydrogen or an sbp member.

11. The compound of claim 10 wherein A has the formula:

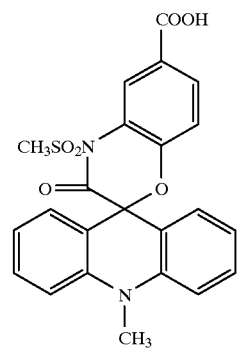

* * * * *